(12) United States Patent
Weitzner et al.

(10) Patent No.: US 7,959,557 B2
(45) Date of Patent: Jun. 14, 2011

(54) ROBOTIC MEDICAL INSTRUMENT SYSTEM

(75) Inventors: Barry D. Weitzner, Acton, MA (US);
Gary S. Rogers, Wenham, MA (US);
Albert Solbjor, Waltham, MA (US);
Dwight Meglan, Westwood, MA (US);
Robert Ailinger, Norwood, MA (US);
David L. Brock, Natick, MA (US);
Woojin Lee, Hopkinton, MA (US);
David Driscoll, Milton, MA (US)

(73) Assignee: Hansen Medical, Inc., Mountain View, CA (US)

( * ) Notice: Subject to any disclaimer, the term of this patent is extended or adjusted under 35 U.S.C. 154(b) by 1016 days.

(21) Appl. No.: 11/762,726

(22) Filed: Jun. 13, 2007

(65) Prior Publication Data
US 2007/0238924 A1 Oct. 11, 2007

Related U.S. Application Data

(63) Continuation of application No. 10/639,785, filed on Aug. 12, 2003.

(60) Provisional application No. 60/403,621, filed on Aug. 14, 2002.

(51) Int. Cl.
*A61B 1/005* (2006.01)

(52) U.S. Cl. ......... 600/102; 600/117; 600/118; 128/898

(58) Field of Classification Search ............ 128/898; 600/102, 117, 118; 700/245, 257, 264; 901/2, 901/8, 31
See application file for complete search history.

(56) References Cited

U.S. PATENT DOCUMENTS

| 2,978,118 A | 4/1961 | Goertz et al. |
| 3,190,286 A | 6/1965 | Stokes |
| 3,923,166 A | 12/1975 | Fletcher et al. |
| 4,604,016 A | 8/1986 | Joyce |
| 4,654,024 A | 3/1987 | Crittenden et al. |
| 4,750,475 A | 6/1988 | Yoshihashi |

(Continued)

FOREIGN PATENT DOCUMENTS

EP 0683016 A1 5/1995

(Continued)

OTHER PUBLICATIONS

Davies, B.L., et al., "A Surgeon Robot for Prostatectomies". Center for Robotics, Imperial College of Science, *IEEE*, Mar. 1991.

(Continued)

*Primary Examiner* — Henry M Johnson, III
*Assistant Examiner* — Aaron Roane
(74) *Attorney, Agent, or Firm* — Vista IP Law Group LLP

(57) ABSTRACT

A method of performing a medical procedure on a patient comprises introducing a medical instrument into a patient (e.g., percutaneously), conveying control signals from a remote controller to a drive unit, and operating the drive unit in accordance with the control signals to actuate the tool located on the medical instrument to secure a stent to an anatomical vessel (e.g., a blood vessel, such as an abdominal aorta). The tool may be a sewing tool that is controlled to stitch the stent to the anatomical vessel. In one method, the control signals are conveyed from the remote controller to the drive unit in response to user commands. The user commands may be movements made at a user interface that correspond to movements of the medical instrument.

21 Claims, 19 Drawing Sheets

U.S. PATENT DOCUMENTS

| | | |
|---|---|---|
| 4,853,874 A | 8/1989 | Iwamoto et al. |
| 4,930,494 A | 6/1990 | Takehana et al. |
| 4,941,454 A | 7/1990 | Wood et al. |
| 4,977,886 A | 12/1990 | Takehana et al. |
| 4,979,949 A | 12/1990 | Matsen, III et al. |
| 5,052,402 A | 10/1991 | Bencini et al. |
| 5,072,361 A | 12/1991 | Davis et al. |
| 5,078,140 A | 1/1992 | Kwoh |
| 5,084,054 A | 1/1992 | Bencini et al. |
| 5,086,401 A | 2/1992 | Glassman et al. |
| 5,116,180 A | 5/1992 | Fung et al. |
| 5,154,717 A | 10/1992 | Matsen, III et al. |
| 5,172,700 A | 12/1992 | Bencini et al. |
| 5,184,601 A | 2/1993 | Putman |
| 5,209,747 A | 5/1993 | Knoepfler |
| 5,217,003 A | 6/1993 | Wilk |
| 5,236,432 A | 8/1993 | Matsen, III et al. |
| 5,238,005 A | 8/1993 | Imran |
| 5,254,130 A | 10/1993 | Poncet et al. |
| 5,271,381 A | 12/1993 | Ailenger et al. |
| 5,287,861 A | 2/1994 | Wilk |
| 5,299,288 A | 3/1994 | Glassman et al. |
| 5,337,732 A | 8/1994 | Grundfest et al. |
| 5,339,799 A | 8/1994 | Kami et al. |
| 5,347,987 A | 9/1994 | Feldstein et al. |
| 5,350,355 A | 9/1994 | Sklar |
| 5,354,311 A | 10/1994 | Kambin et al. |
| 5,368,015 A | 11/1994 | Wilk |
| 5,372,147 A | 12/1994 | Lathrop, Jr. et al. |
| 5,382,885 A | 1/1995 | Salcudean et al. |
| 5,395,367 A | 3/1995 | Wilk |
| 5,397,323 A | 3/1995 | Taylor et al. |
| 5,402,801 A | 4/1995 | Taylor |
| 5,409,019 A | 4/1995 | Wilk |
| 5,410,638 A | 4/1995 | Colgate et al. |
| 5,417,210 A | 5/1995 | Funda et al. |
| 5,429,144 A | 7/1995 | Wilk |
| 5,441,505 A | 8/1995 | Nakimura |
| 5,467,763 A | 11/1995 | McMahon et al. |
| 5,492,131 A | 2/1996 | Galel |
| 5,497,784 A | 3/1996 | Imran |
| 5,515,478 A | 5/1996 | Wang |
| 5,520,644 A | 5/1996 | Imran |
| 5,524,180 A | 6/1996 | Wang et al. |
| 5,527,279 A | 6/1996 | Imran |
| 5,540,649 A | 7/1996 | Bonnell et al. |
| 5,553,198 A | 9/1996 | Wang et al. |
| 5,572,999 A | 11/1996 | Funda et al. |
| 5,586,968 A | 12/1996 | Grundl et al. |
| 5,618,294 A | 4/1997 | Aust et al. |
| 5,620,415 A | 4/1997 | Lucey et al. |
| 5,624,398 A | 4/1997 | Smith et al. |
| 5,626,553 A | 5/1997 | Frassica et al. |
| 5,626,595 A | 5/1997 | Sklar et al. |
| 5,631,973 A | 5/1997 | Green |
| 5,632,758 A | 5/1997 | Sklar |
| 5,643,294 A | 7/1997 | Tovey et al. |
| 5,649,956 A | 7/1997 | Jensen et al. |
| 5,657,429 A | 8/1997 | Wang et al. |
| 5,662,587 A | 9/1997 | Grundfest et al. |
| 5,667,476 A | 9/1997 | Frassica et al. |
| 5,754,741 A | 5/1998 | Wang et al. |
| 5,762,458 A | 6/1998 | Wang et al. |
| 5,766,196 A | 6/1998 | Griffiths |
| 5,784,542 A | 7/1998 | Ohm et al. |
| 5,792,135 A | 8/1998 | Madhani et al. |
| 5,800,333 A | 9/1998 | Liprie |
| 5,800,423 A | 9/1998 | Jensen |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,814,038 A | 9/1998 | Jensen et al. |
| 5,815,640 A | 9/1998 | Wang et al. |
| 5,817,084 A | 10/1998 | Jensen et al. |
| 5,821,920 A | 10/1998 | Rosenberg et al. |
| 5,823,993 A | 10/1998 | Lemelson |
| 5,825,982 A | 10/1998 | Wright et al. |
| 5,828,197 A | 10/1998 | Martin et al. |
| 5,833,656 A | 11/1998 | Smith et al. |
| 5,845,646 A | 12/1998 | Lemelson |
| 5,855,553 A | 1/1999 | Tajima et al. |
| 5,855,583 A | 1/1999 | Wang et al. |
| 5,860,992 A | 1/1999 | Daniel et al. |
| 5,861,024 A | 1/1999 | Rashidi |
| 5,876,325 A | 3/1999 | Mizuno et al. |
| 5,878,193 A | 3/1999 | Wang et al. |
| 5,907,664 A | 5/1999 | Wang et al. |
| 5,928,248 A | 7/1999 | Acker |
| 5,931,832 A | 8/1999 | Jensen |
| 5,954,692 A | 9/1999 | Smith et al. |
| 5,964,717 A | 10/1999 | Gottlieb et al. |
| 5,976,122 A | 11/1999 | Madhani et al. |
| 6,001,108 A | 12/1999 | Wang et al. |
| 6,007,550 A | 12/1999 | Wang et al. |
| 6,007,560 A | 12/1999 | Gottlieb et al. |
| 6,024,695 A | 2/2000 | Taylor et al. |
| 6,033,378 A | 3/2000 | Lundquist et al. |
| 6,036,636 A | 3/2000 | Motoki et al. |
| 6,058,323 A | 5/2000 | Lemelson |
| 6,063,095 A | 5/2000 | Wang et al. |
| 6,080,181 A | 6/2000 | Jensen et al. |
| 6,096,004 A | 8/2000 | Meglan et al. |
| 6,102,850 A | 8/2000 | Wang et al. |
| 6,102,920 A | 8/2000 | Sullivan et al. |
| 6,106,511 A | 8/2000 | Jensen |
| 6,120,433 A | 9/2000 | Mizuno et al. |
| 6,132,368 A | 10/2000 | Cooper |
| 6,132,441 A | 10/2000 | Grace |
| 6,146,355 A | 11/2000 | Biggs |
| 6,197,017 B1 | 3/2001 | Brock et al. |
| 6,203,525 B1 | 3/2001 | Whayne et al. |
| 6,206,903 B1 | 3/2001 | Ramans |
| 6,221,070 B1 | 4/2001 | Tu et al. |
| 6,223,100 B1 | 4/2001 | Green |
| 6,231,565 B1 | 5/2001 | Tovey et al. |
| 6,233,504 B1 | 5/2001 | Das et al. |
| 6,235,051 B1 * | 5/2001 | Murphy .................. 623/1.12 |
| 6,246,200 B1 | 6/2001 | Blumenkranz et al. |
| 6,290,675 B1 | 9/2001 | Vujanic et al. |
| 6,301,526 B1 | 10/2001 | Kim et al. |
| 6,309,397 B1 | 10/2001 | Julian et al. |
| 6,312,435 B1 | 11/2001 | Wallace et al. |
| 6,325,808 B1 | 12/2001 | Bernard et al. |
| 6,331,181 B1 | 12/2001 | Tierney et al. |
| 6,332,889 B1 | 12/2001 | Sancoff et al. |
| 6,341,231 B1 | 1/2002 | Ferre et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,369,834 B1 | 4/2002 | Zilles et al. |
| 6,371,907 B1 | 4/2002 | Hasegawa et al. |
| 6,375,471 B1 | 4/2002 | Wendlandt et al. |
| 6,377,011 B1 | 4/2002 | Ben-Ur |
| 6,385,509 B2 | 5/2002 | Das et al. |
| 6,394,998 B1 | 5/2002 | Wallace et al. |
| 6,398,726 B1 | 6/2002 | Ramans et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,565,554 B1 | 5/2003 | Niemeyer |
| 6,569,084 B1 | 5/2003 | Mizuno et al. |
| 6,587,750 B2 | 7/2003 | Gerbi et al. |
| 6,594,552 B1 | 7/2003 | Nowlin et al. |
| 6,620,173 B2 | 9/2003 | Gerbi et al. |

| | | |
|---|---|---|
| 6,645,196 B1 | 11/2003 | Nixon et al. |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz et al. |
| 6,793,653 B2 | 9/2004 | Sanchez et al. |
| 6,799,065 B1 | 9/2004 | Niemeyer |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 | 1/2005 | Morley et al. |
| 6,852,107 B2 | 2/2005 | Wang et al. |
| 6,860,877 B1 | 3/2005 | Sanchez et al. |
| 6,911,916 B1 | 6/2005 | Wang et al. |
| 6,936,001 B1 | 8/2005 | Snow |
| 6,951,535 B2 | 10/2005 | Ghodoussi et al. |
| 6,994,708 B2 | 2/2006 | Manzo |
| 7,025,064 B2 | 4/2006 | Wang et al. |

FOREIGN PATENT DOCUMENTS

| | | |
|---|---|---|
| EP | 0776738 A2 | 6/1997 |
| JP | 6-114000 | 4/1994 |
| WO | WO 98/25666 | 6/1998 |
| WO | WO 00/60521 | 10/2000 |
| WO | WO 00/67640 | 11/2000 |
| WO | WO 02/74178 | 2/2002 |

OTHER PUBLICATIONS

Dohi, T., "Medical Application of Robotics Mechatronics", *International Biomedical Engineering Days*, Aug. 1992.

Ikuta, et al., "Shape Memory Alloy Servo Actuator System With Electric Resistance Feedback and Application for Active Endoscope", *IEEE*, CH2555-1/88/0000/0427-430 Apr. 1988.

Kwoh, Y.S., et al., "A Robot With Improved Absolute Positioning Accuracy for CT Guided Stereotactic Brain Surgery," *IEEE Transactions on Biomedical Engineering*, 35 (2), Feb. 1998.

Sabatini, A.M., et al., "Force Feedback-Based Telemicromanipulation for Robot Surgery on Soft Tissue", *IEEE Engineering in Medicine & Biology Society*, Nov. 1989.

Thring, M.W., "Robots and Telechirs: Manipulators With Memory; Remote Manipulators; Machine Limbs for the Handicapped", Sep. 21, 1983, by Ellis Horwood Limited.

\* cited by examiner

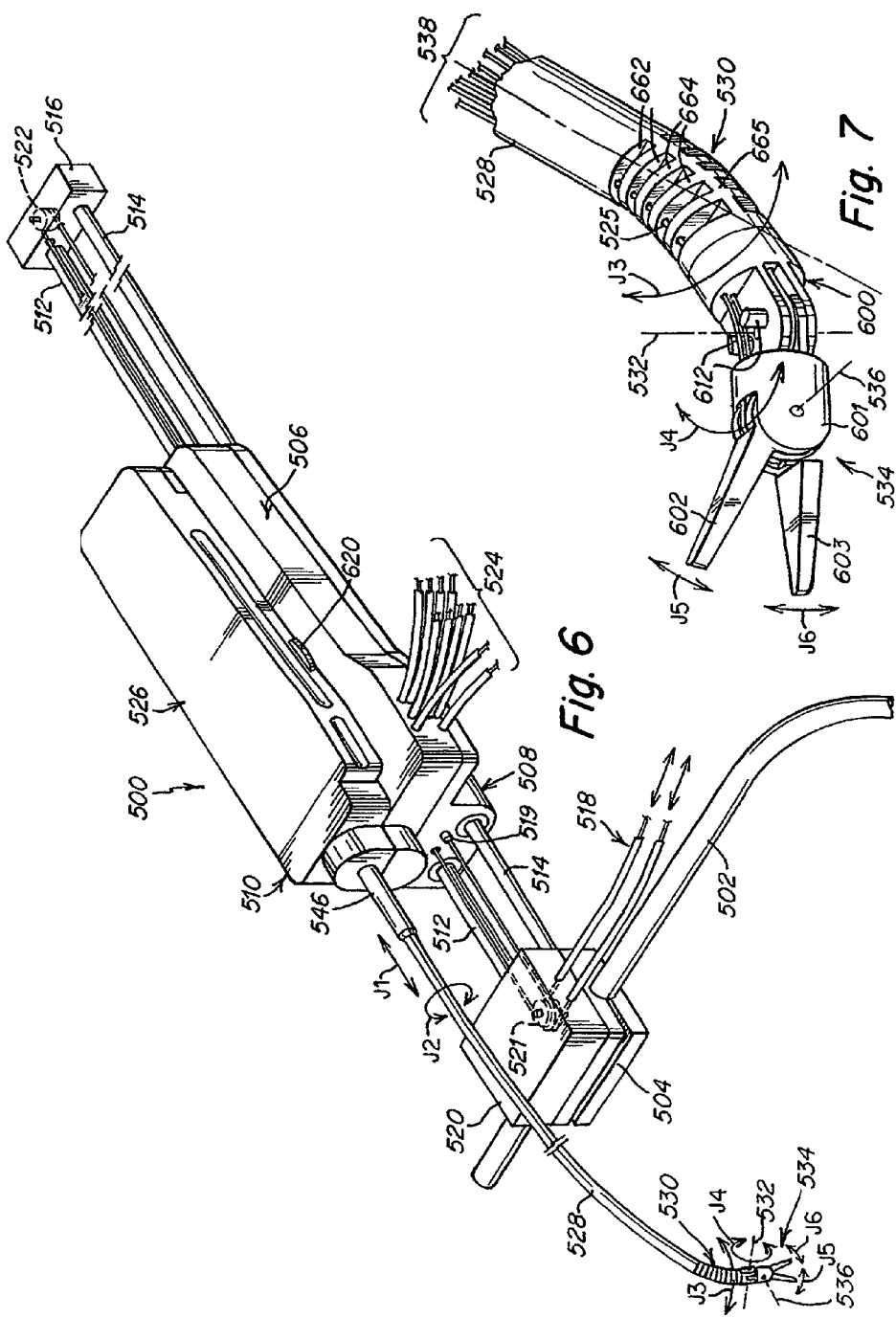

ROBOTIC MEDICAL INSTRUMENT SYSTEM

RELATED APPLICATIONS

This application is a continuation of U.S. application Ser. No. 10/639,785, filed Aug. 12, 2003, which claims benefit of priority from U.S. application Ser. No. 60/403,621, filed Aug. 14, 2002. This application is also related to U.S. application Ser. No. 11/762,722, Ser. No. 11/762,723, Ser. No. 11/762,730, Ser. No. 11/762,734, and Ser. No. 11/762,737, all of which were filed on Jun. 13, 2007, and the entire disclosures of all of which are expressly incorporated herein by reference.

BACKGROUND OF THE INVENTION

Robotically controlled surgical instruments are usually controlled from a master station at which a surgeon or other medical practitioner is situated. The master station may include one or more input devices manipulated by the user for, in turn, controlling, at an operative site, respective instruments used in performing a surgical procedure or application.

SUMMARY OF THE INVENTION

In accordance with the present inventions, a method of performing a medical procedure on a patient is provided. The method comprises introducing a medical instrument into a patient (e.g., percutaneously), conveying control signals from a remote controller to a drive unit, and operating the drive unit in accordance with the control signals to actuate the tool located on the medical instrument to secure a stent to an anatomical vessel (e.g., a blood vessel, such as an abdominal aorta). The tool may be a sewing tool that is controlled to stitch the stent to the anatomical vessel. By way of non-limiting example, the stent may be secured within the anatomical vessel, and the medical instrument may be external to the anatomical vessel when the tool is operated to secure the stent to the anatomical vessel.

In one method, the medical instrument is introduced into the patient by operating the drive unit in accordance with the control signals. Another method further comprises operating the drive unit in accordance with the control signals to advance the medical instrument within the anatomical vessel. Still another method further comprises operating the drive unit in accordance with the control signals to introduce the stent adjacent the anatomical vessel. In yet another method, the control signals are conveyed from the remote controller to the drive unit in response to user commands. The user commands may be movements made at a user interface that correspond to movements of the medical instrument. Yet another method may comprise operating the drive unit in accordance with the control signals to advance another medical instrument to the target region, and to actuate the tool on the medical instrument and another tool on the other medical instrument in unison to secure the stent to the anatomical vessel. In this case, the medical instrument may be located within the anatomical vessel and the other medical instrument may be located outside the anatomical vessel when the tool and the other tool are operated in unison to secure the stent to the anatomical vessel.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 6 is a perspective view of another embodiment of the present invention;

FIG. 7 is an enlarged detail perspective view of the tool;

DETAILED DESCRIPTION OF THE INVENTION

A description of preferred embodiments of the invention follows.

Figure 1:
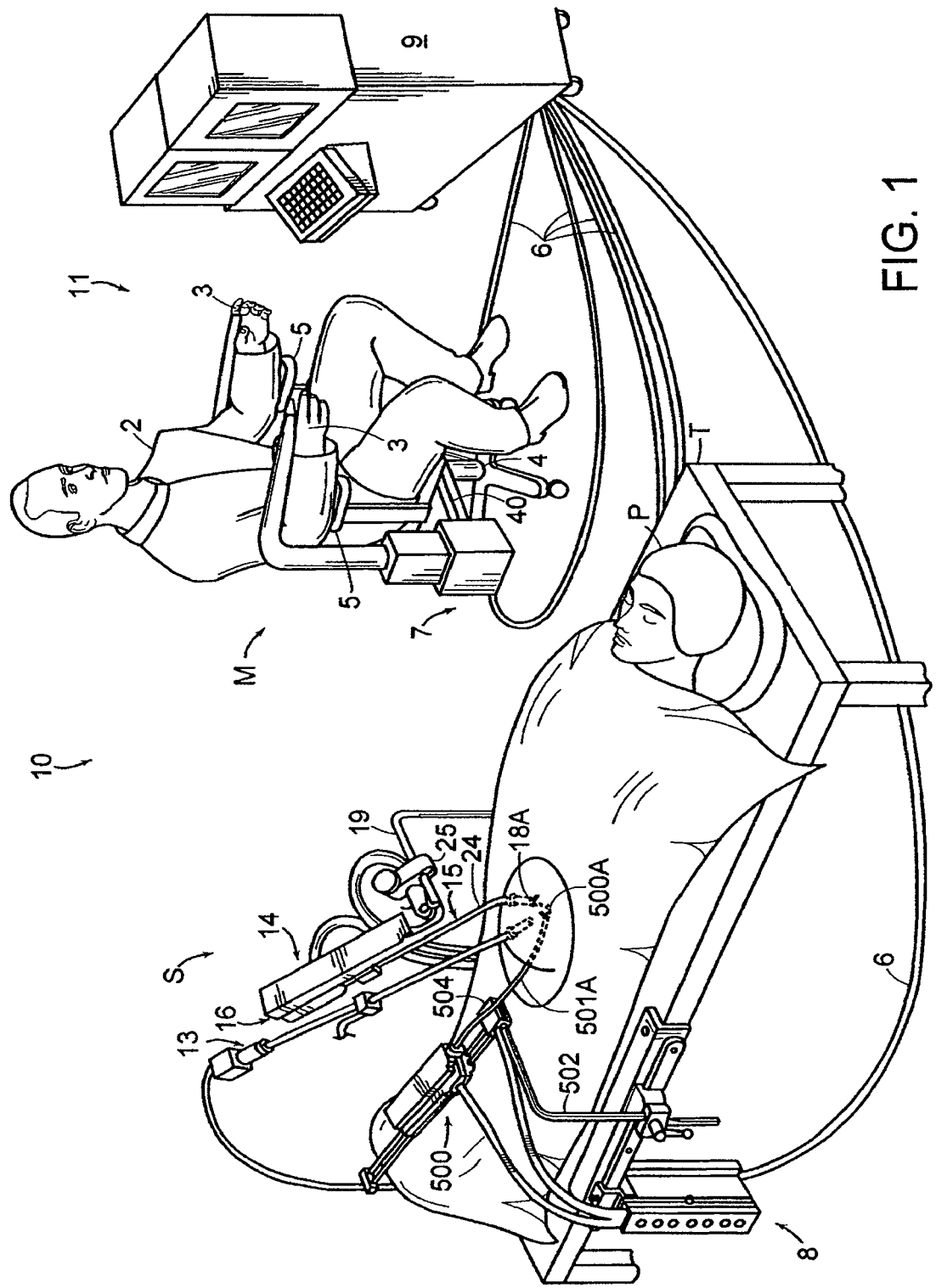
FIG. 1 is a perspective view of one embodiment of a robotic surgical system in which the principles of the present invention are applied.

FIG. 1 is a perspective view of one embodiment of a robotic surgical system in which the principles of the present invention are applied. FIG. 1 illustrates a surgical instrument system 10 that includes a master M at which a surgeon 2 manipulates an input device, and a slave station S at which is disposed a surgical instrument. In FIG. 1 the input device is illustrated at 3 being manipulated by the hand or hands of the surgeon. The surgeon is illustrated as seated in a comfortable chair 4. The forearms of the surgeon are typically resting upon armrests 5.

FIG. 1 illustrates a master assembly 7 associated with the master station M and a slave assembly or drive unit 8 associated with the slave station S. Assemblies 7 and 8 are interconnected by means of cabling 6 with a controller 9. As illustrated in FIG. 1, controller 9 typically has associated therewith one or more displays and a keyboard. Reference is also made to, for example, the aforementioned U.S. Ser. No. 10/014,143, for further detailed descriptions of the robotic and computer controller operation and associated operating algorithm.

As noted in FIG. 1, the drive unit 8 is remote from the operative site and is preferably positioned a distance away from the sterile field. The drive unit 8 is controlled by a computer system, part of the controller 9. The master station M may also be referred to as a user interface vis-vis the controller 9. Commands issued at the user interface are translated by the computer into an electronically driven motion in the drive unit 8. The surgical instrument, which is tethered to the drive unit through the cabling connections, produces the desired replicated motion. FIG. 1, of course, also illustrates an operating table T upon which the patient P is placed.

Figure 4:
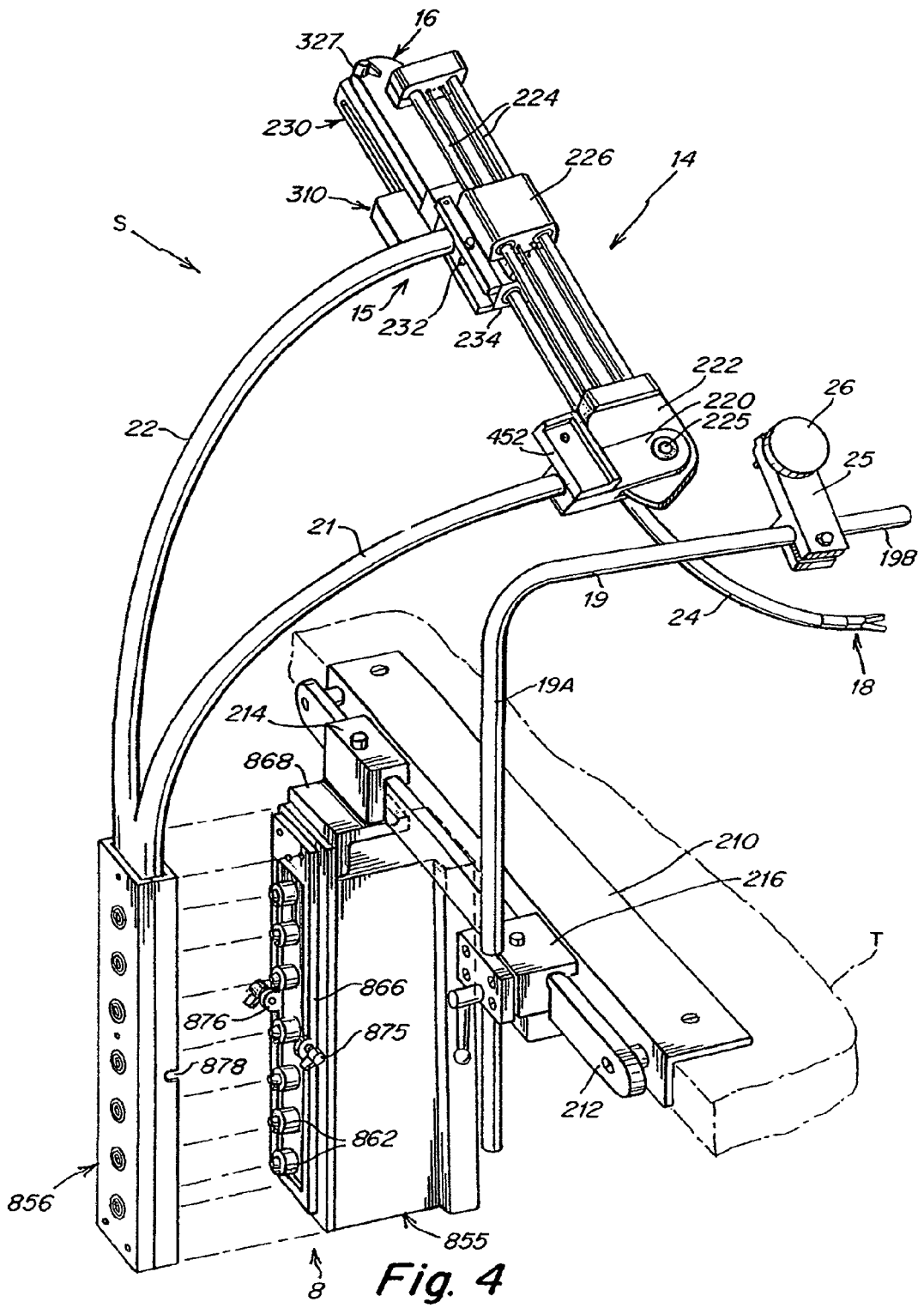
FIG. 4 is an exploded perspective view of another version of the cable drive mechanism and tool in accordance with the present invention.

FIG. 1 illustrates both a flexible system and a rigid system. Only one drive unit is depicted, it being understood that there is also a drive unit associated with the rigid instrument system such as shown in FIG. 4. Each of the drive units is controlled from cabling that couples from the controller. This is electrical cabling that drives corresponding motors in each drive unit.

Thus, the controller couples between the master station M and the slave station S and is operated in accordance with a computer algorithm. The controller receives a command from the input device 3 and controls the movement of the surgical instrument so as to replicate the input manipulation. The controller may also receive commands from the master station for controlling instrument interchange.

With further reference to FIG. 1, associated with the patient P is the surgical instrument 14, which in the illustrated embodiment actually comprises two separate instruments one rigid and one flexible, along with an endoscope E. The endoscope includes a camera to remotely view the operative site. The camera may be mounted on the distal end of the instrument insert, or may be positioned away from the site to provide additional perspective on the surgical operation. In certain situations, it may be desirable to provide the endoscope through an opening other than the one used by the rigid surgical instrument. In this regard, in FIG. 1 three separate ingress locations are shown, two for accommodating the rigid surgical instrument and the endoscope, and the third accommodates the flexible instrument through a natural body orifice. A drape is also shown.

The viewing endoscope may also be formed integral with the instrument whether it be a rigid instrument or a flexible instrument. The optics and camera may be mounted directly on the distal part of the instrument such as at or adjacent the end effector. In particular, with respect to a flexible instrument the optics and camera may be supported at the distal end of the instrument.

In FIG. 1, as indicated previously two separate instruments are depicted, a rigid instrument system 14 and a flexible instrument system 500. In the rigid instrument system there is an instrument insert that carries at its distal end an end effector 18A entering the anatomy through a small incision. This may be for the purpose of providing access to the area about the bowel or bladder, for example. In the flexible instrument system there is a flexible and bendable instrument section terminating at the end effector 500A, and entering the anatomy, for example, through a natural body orifice such as through the anus in the case of a bowel procedure.

An end effector is usually associated with each of the instrument systems. In FIG. 1 this is illustrated by the end effectors 18A and 500A. These can take on a variety of different form such as scissors, graspers or needle drivers. Both of the medical instrument members comprise active work elements at respective member working ends and are usually disposed at opposite sides of an anatomic wall. By "active", reference is made to end effectors that are useable in performing a surgical procedure or application and that are capable of being manipulated from a master station such as from a surgeon controlled input device.

The instrument system 14 is generally comprised of two basic components, including a surgical adaptor or guide 15 and an instrument insert 16. FIG. 1 illustrates the surgical adaptor 15, which is comprised primarily of the guide tube 24, but also includes a mechanical interface that interfaces with a corresponding mechanical interface of the instrument itself. In FIG. 1 the instrument 14 is not clearly illustrated but extends through the guide tube 24. The instrument 14 carries at its distal end the instrument member or insert. The surgical adaptor 15 is basically a passive mechanical device, driven by the attached cable array.

In FIG. 1 there is illustrated cabling that couples from the instrument 14 to the drive unit. The cabling 22 is preferably detachable from the drive unit. Furthermore, the surgical adaptor 15 may be of relatively simple construction. It may thus be designed for particular surgical applications such as abdominal, cardiac, spinal, arthroscopic, sinus, neural, etc. As indicated previously, the instrument 14 couples to the adaptor 15 and essentially provides a means for exchanging the instrument tools. The tools may include, for example, forceps, scissors, needle drivers, electrocautery etc. Other tool interchanges are also shown in further drawings herein.

Referring still to FIG. 1, the surgical system 10 includes a surgeon's interface 11, computation system or controller 9, drive unit 8 and the surgical instrument 14. The surgical system 10, as mentioned previously, is comprised of an adaptor or guide 15 and the instrument insert 16. The system is used by positioning the instrument, which is inserted through the surgical adaptor or guide 15. During use, a surgeon may manipulate the input device 3 at the surgeon's interface 11, to affect desired motion of the distal end of the instrument within the patient. The movement of the handle or hand assembly at input device 3 is interpreted by the controller 9 to control the movement of the guide tube 24, instrument, and, when an articulating instrument is used, the end effector or tool 18A. Also, movements at the master station may control instrument exchange.

The surgical instrument 14, along with the guide tube 24 is mounted on a rigid post 19 which is illustrated in FIG. 1 as removably affixed to the surgical table T. This mounting arrangement permits the instrument to remain fixed relative to the patient even if the table is repositioned. As indicated previously, connecting between the surgical instrument 14 and the drive units 8, are cablings. These include two mechanical cable-in-conduit bundles. These cable bundles may terminate at two connection modules, not illustrated in FIG. 1, which removably attach to the rigid instrument drive unit 8. Although two cable bundles are described here, it is to be understood that more or fewer cable bundles may be used. Also, the drive unit 8 is preferably located outside the sterile field, although it may be draped with a sterile barrier so that it may be operated within the sterile field.

In the preferred technique for setting up the system, and with reference to FIG. 1, the surgical instrument 14 is inserted into the patient through an incision or opening. The instrument 14 is then mounted to the rigid post 19 using a mounting bracket. The cable bundle or bundles are then passed away from the operative area to the drive unit. The connection modules of the cable bundles are then engaged into the drive unit. The separate instrument members of instrument 14 are then selectively passed through the guide tube 24. This action is in accordance with the interchangeable instrument concepts also described herein.

The instrument 14 is controlled by the input device 3, which is be manipulated by the surgeon. Movement of the hand assembly produces proportional movement of the instrument 14 through the coordinating action of the controller 9. It is typical for the movement of a single hand control to control movement of a single instrument. However, FIG. 1 shows a second input device that is used to control an additional instrument. Accordingly, in FIG. 1 two input devices are illustrated and two corresponding instruments. These input devices are usually for left and right hand control by the surgeon. Many other forms of input device control may also be used. For example, instead of finger graspers a joystick arrangement may be used.

The surgeon's interface 11 is in electrical communication with the controller 9. This electrical control is primarily by way of the cabling 6 illustrated in FIG. 1 coupling from the bottom of the master assembly 7. Cabling 6 also couples from the controller 9 to the actuation or drive units. This cabling 6 is electrical cabling. Each of the actuation or drive units, however, is in mechanical communication with the corresponding instrument. The mechanical communication with the instrument allows the electromechanical components to be removed from the operative region, and preferably from the sterile field. The surgical instrument provides a number of independent motions, or degrees-of-freedom, when an articulating type instrument such as a tool, gripper, etc. is used. These degrees-of-freedom are provided by both the guide tube 24 and the instrument insert.

Figures 15, 16:
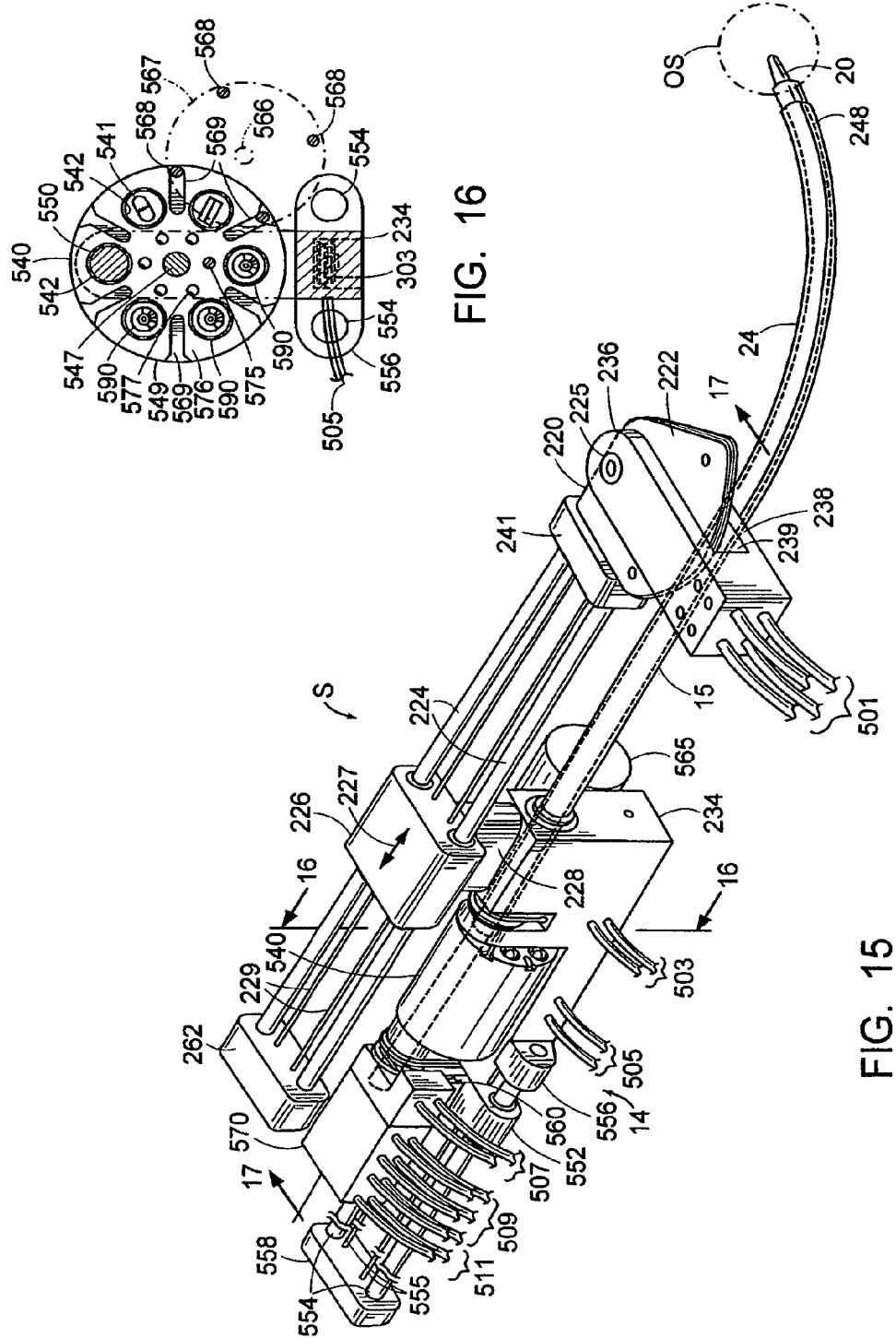
FIG. 15 is a perspective view at the slave station of the system of FIG. 1 illustrating the interchangeable instrument concepts.
FIG. 16 is a cross-sectional view through the storage chamber and as taken along line 16-16 of FIG. 15.
Figure 17:
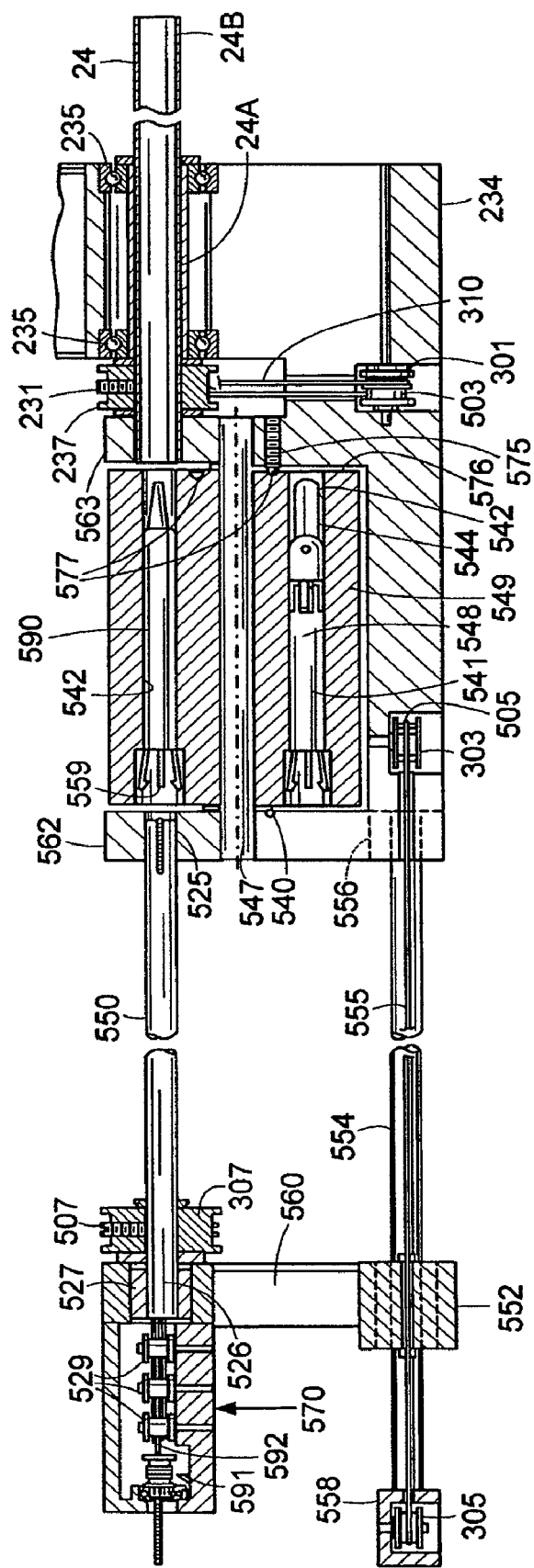
FIG. 17 is a longitudinal cross-sectional view, as taken along line 17-17 of FIG. 15, and showing both a stored articulating instrument and a stored fluid dispensing.

FIG. 1 shows primarily the overall surgical system. FIGS. 15-17 show further details particularly of the interchangeable instrument concepts as applied to this system. The rigid instrument part of the system is adapted to provide seven degrees-of-freedom when an articulating tool is used such as the tool 18A shown in FIG. 1. Three of the degrees-of-freedom are provided by motions of the adaptor 15, while four degrees-of-freedom may be provided by motions of the instrument. As will be described in detail later, the adaptor is remotely controllable so that it pivots, translates linearly, and has its guide tube rotate. The instrument insert also rotates (via rotation of the instrument driver), pivots at its wrist, and has two jaw motions at the tool.

Figure 2:
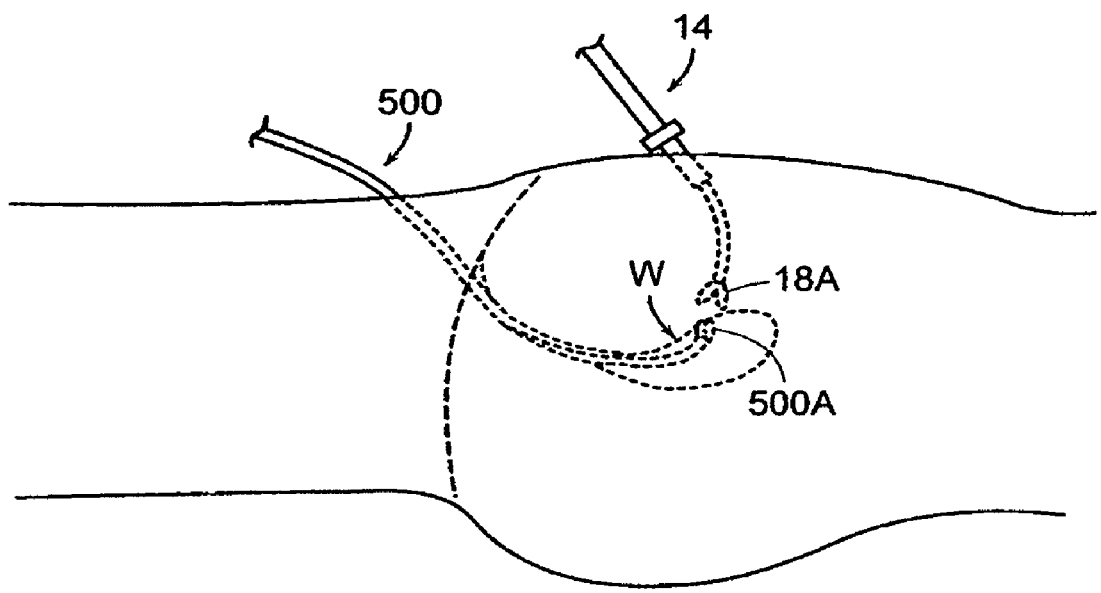
FIG. 2 schematically illustrates a surgical procedure using intralumenal and extralumenal instruments, one flexible and one rigid.

Now, mention has been made of bowel and bladder procedures illustrated schematically in FIG. 2. This shows the two separately controlled instruments including rigid instrument system 14 that may be engaged laparoscopically through a small incision, and flexible instrument system 500 that may be engaged through the anus in the case of a bowel procedure or the urethra in the case of a bladder procedure. FIG. 2 also shows the respective end effectors 18A and 500A. These end effectors are shown positioned on either side of an anatomic wall W shown schematically in dotted outline in FIG. 2.

Figure 3:
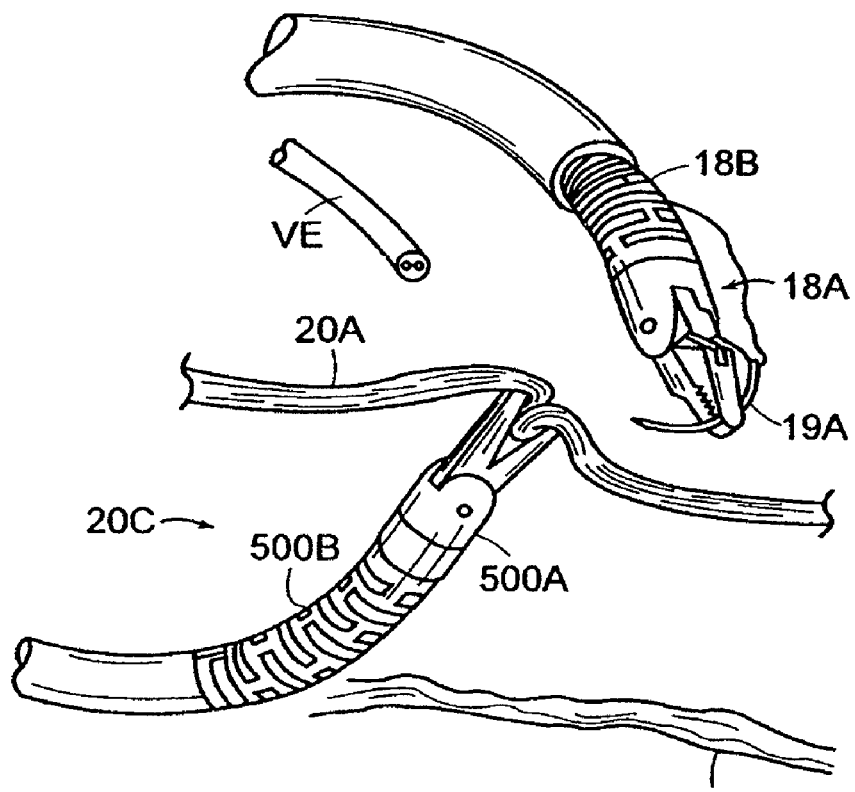
FIG. 3 illustrates respective end effectors of rigid and flexible instruments used in performing a suturing procedure at a wall of a lumen.

Refer now also to FIG. 3 for an illustration of further details showing the end effectors 18A and 500A positioned to perform a suturing step with a needle 19A being grasped by the end effector 18A. The rigid instrument has been passed through a small incision and is positioned outside the vessel wall 20A. The flexible instrument with end effector 500A is positioned within the lumen 20C between walls 20A and 20B. The end effector 500A is shown grasping a tissue at the wall, assisting in the suturing step. In FIG. 3 both of the instruments include at their distal ends, proximal of the end effectors, bendable sections 18B and 500B. Each of these bendable sections or segments is remotely controllable from the master input devices, allowing additional degrees of freedom of motion of the respective end effectors. The end effectors of both instruments are preferably also remotely computer-controlled from a master station input device or devices. Also, illustrated is a viewing endoscope VE directed at the operative site where the end effectors are acting.

Figure 3A:
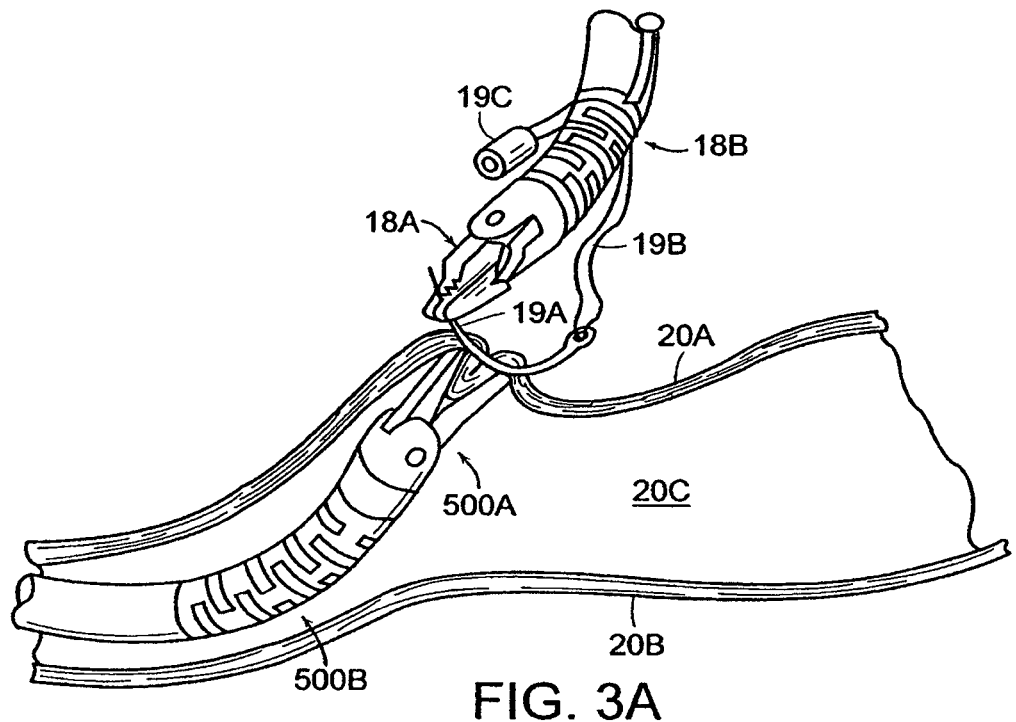
FIG. 3A shows a next step in the suturing process with the needle having punctured the anatomic wall.

Reference is now made to FIG. 3A showing a next step in the suturing procedure. The needle 19A has now passed through the vessel wall 20A. The suture 19B is attached to the end of the needle 19A, as illustrated. In FIG. 3A there is illustrated a viewing endoscope 19C that is attached to the instrument 18 just proximal of the end effector 18A.

Figure 3B:
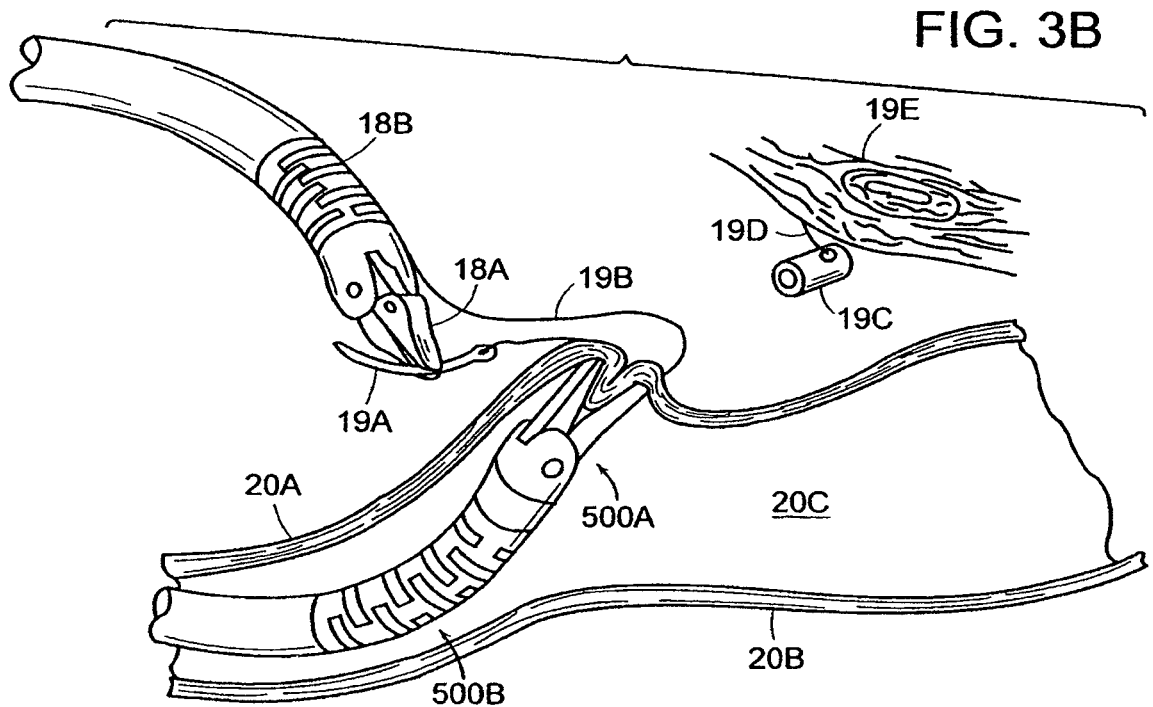
FIG. 3B shows still another suturing step with the suture being pulled through the wall, and further illustrating the placement of a viewing endoscope attached internally.

In FIG. 3B the needle 19A is shown in the next step with the suture 19B having passed through the anatomic wall 20A. In this arrangement the viewing endoscope 19C is shown secured to the chest wall 19E. There may be provided a clamp 19D, or the like for holding the viewing endoscope in place and in a good viewing location for the surgical procedure that is being performed. In both FIGS. 3A and 3B the instrument system 500 is within the lumen 20C, while the instrument system 14 is outside the lumen 20C. The instrument systems 500 within the lumen are usually of the flexible type so as to be able to maneuver through an anatomic body part. The instrument system outside the lumen is illustrated as being of the rigid type but could also be of the flexible type.

Figure 3C:
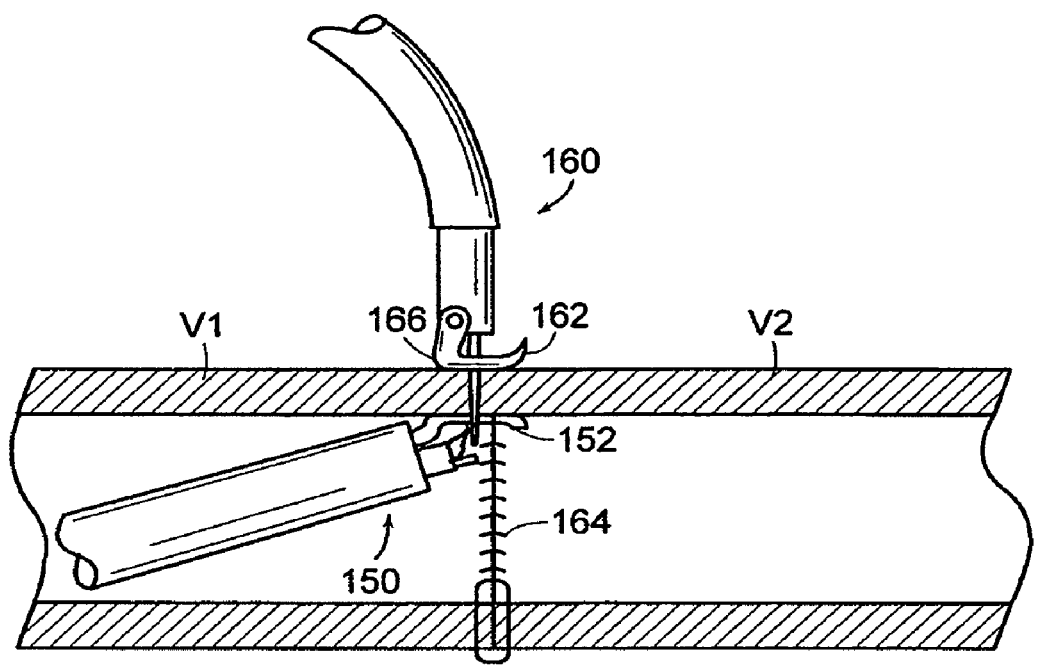
FIG. 3C is a schematic illustration of dual end effectors used in a sewing technique for attaching vessel segments together.

FIG. 3C shows the use of another dual instrument system that is adapted for intralumenal/extralumenal positioning. This particular arrangement is for sewing between two separate vessels V1 ands V2. This procedure may be used in a variety of different types of operations in which it is desirable to secure together two vessels or lumens, end-to-end. For this purpose there are provided two instrument systems, both of which are preferably robotically controlled from a master station input device. The control of the two systems may be under direct surgeon control such as from an input device manipulated by the surgeon, or, alternatively the systems may be automatically controlled so that once a sequence is initiated the ensuing steps are performed automatically. For example in a sewing procedure it may be desirable to position the instrument systems and, once positioned, it may be desirable to initiate a sequence of suturing steps or stitches so that the suturing occurs essentially automatically, with little or no surgeon intervention except for safety concerns.

Now, in FIG. 3C there is illustrated a dual instrument system that includes an internally disposed system 150, and an externally disposed system 160. The system 150 is usually of the flexible type as the instrument shaft has to negotiate a vessel or lumen that typically has non-straight portions. The instrument system 160, on the other hand, may be flexible or rigid, but would usually be rigid as it would enter the anatomy through an incision or percutaneously. In FIG. 3C the instrument systems together define a sewing system including, on the instrument system 150 a hook end effector 152, and on the instrument system 160 a needle end effector 162. Together these instrument systems are adapted to be operated in unison and usually in an automatic manner, although the sewing steps can also be performed under manual control of the surgeon from a master station.

The combination of the instrument systems 150 and 160 provide a sewing technique. The system 150 with its hook end effector 152 cooperates with the needle end effector 162 supported by the instrument system 160. This arrangement may be used to provide a chain stitch. Both of the end effectors are controllable with multiple degrees of freedom. Thus, if the systems are used under manual robotic control the hook end effector 152 is moved in unison with the needle end effector 162 to provide the stitch 164. The needle end effector 162 is adapted to reciprocate relative to its presser foot 166. At the beginning of each stitch, the needle end effector 160 pulls a loop of suture material through the tissue. The hook end effector 150 moves in synchronism with the needle end effector 160 and grabs the loop of suture material before the needle end effector 160 pulls up. The instrument system proceed about the vessel portions and FIG. 3D shows the final stitch 164 that attaches the vessels or lumens together, end-to-end.

Figure 3D:
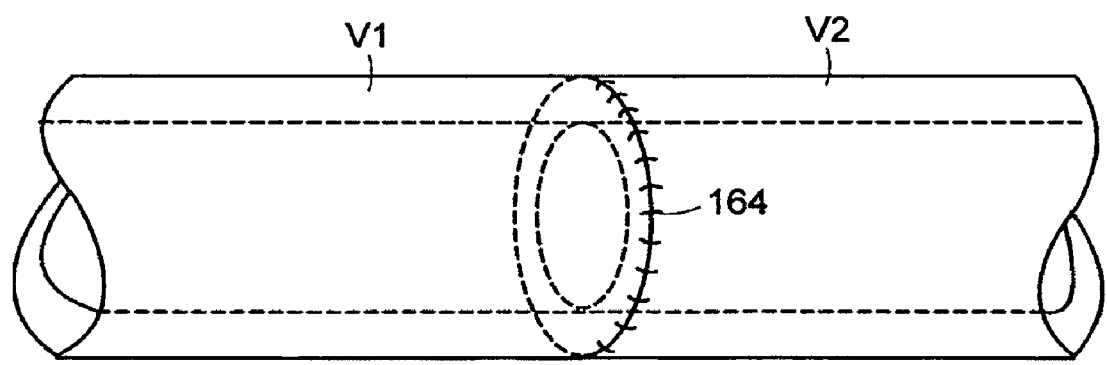
FIG. 3D illustrates the completion of the sewing technique of FIG. 3C.

In connection with the systems shown in FIGS. 3C and 3D these instrument systems may also be controlled automatically and under computer control. In that case, once the instrument systems are in place, sensors associated with each instrument system detects the relative position between them. Then the computer at the controller that is disposed between master and slave stations, controls the instrument systems in unison to perform the stitching action. In other words the computer controls the action of the needle end effector and hook end effector to perform the stitch such as a chain stitch.

In the arrangement shown in FIGS. 3C and 3D the needle end effector is shown outside the lumen while the hook end effector is shown inside the lumen. In an alternate embodiment the positions of the instruments may be interchanged do the hook end effector is outside the lumen and the needle end effector is inside the lumen. The positioning between the end effectors can be controlled by sensing electromagnetic signals associated with sensors associated with each instrument system. The stitching sequences described can provide a variety of different stitch patterns. Inversion or eversion of sewed edges can be provided depending upon the particular surgical procedure being performed. For example, for cardiac procedures a slight inversion of the stitch is desired.

Figure 3E:
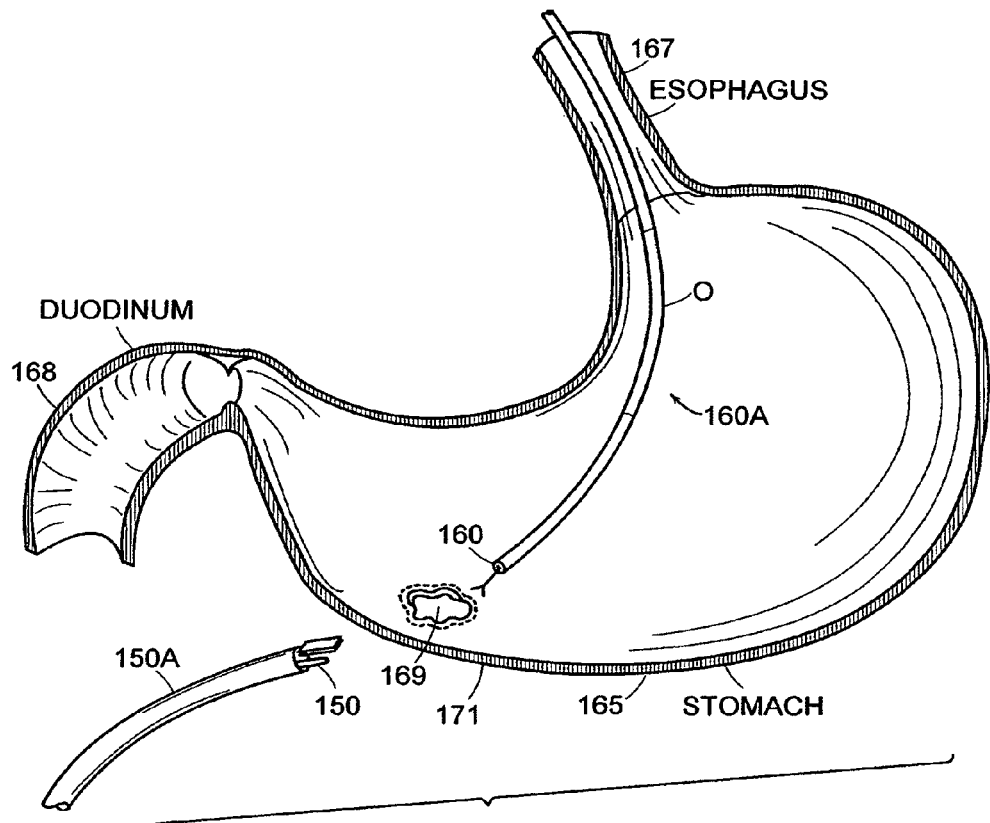
FIG. 3E illustrates a surgical procedure in the stomach using dual instruments, a flexible instrument passing into the stomach and either a rigid or flexible instrument outside the stomach wall.
Figure 3F:
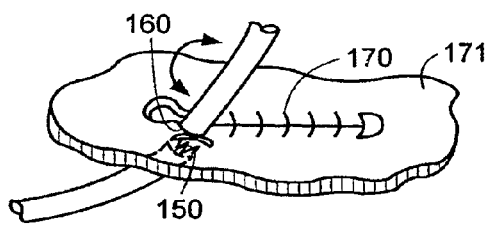
FIG. 3F schematically shows the end of the sewing or suturing technique at the stomach wall.

FIG. 3E illustrates a surgical procedure in the stomach using dual instruments, a flexible instrument passing into the stomach and either a rigid or flexible instrument outside the stomach wall. FIG. 3F schematically shows the end of the sewing or suturing technique at the stomach wall. The flexible instrument system 160A passes through the esophagus 167 entering initially through the patient's mouth. The outlet from the stomach is at the duodenum 168. This flexible instrument system is illustrated as having an operative segment O controlled by the surgeon in a telerobotic manner to control bending at that segment for guidance of the distal end effector 160. An outside instrument system 150 is also illustrated which may be either a flexible or rigid instrument system. This is illustrated in FIG. 3E by system 150A carrying the end effector 150. In FIGS. 3E and 3F the end effectors may be the same as shown in FIGS. 3C and 3D used in performing a sewing or suturing operation. The instrument systems are controlled to perform the sewing or suturing action forming stitches 170 as illustrated in FIG. 3F. This stitching action closes the hole 169.

FIGS. 3E and 3D illustrate a surgical procedure on the stomach 165 particularly at the stomach wall 171. An ulcerated hole 169 is disclosed and it is the purpose of the instrument system shown to close up this hole by means of a sewing or suturing technique employing the instrument systems 150A and 160A. The procedure shown in FIGS. 3E and 3F can be performed manually from the master station or can be performed automatically under computer control initiated from the master station. The same or a similar procedure can also be used for gastric ulcers or for repairing a bowel wall defect.

Figure 3G:
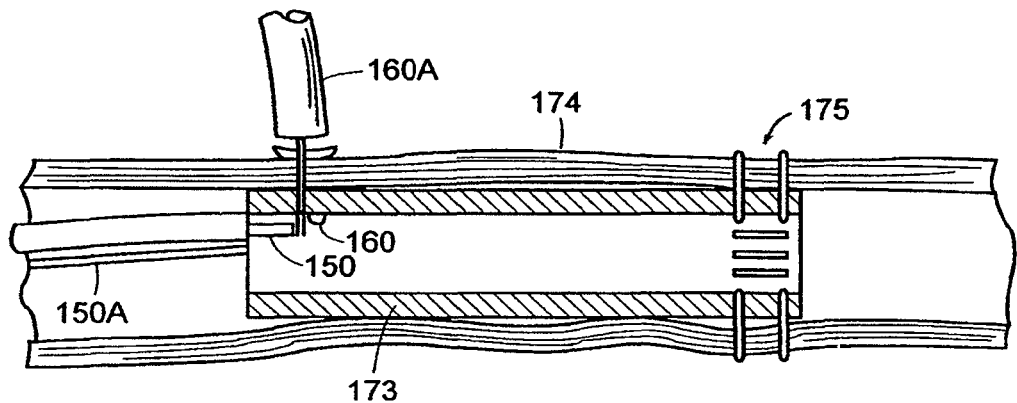
FIG. 3G illustrates the dual instruments used for securing or re-securing an internal object such as a stent in an artery, vein, or other anatomic lumen or vessel.

FIG. 3G shows still another technique that can be practiced with the instrument systems described herein. In FIG. 3G the same reference characters are used to identify similar components as previously described in connection with FIGS. 3C and 3D. In this instance an object is being stitched within the body vessel 174. The object may be, for example, a stent 173 that is being secured or re-secured within the vessel walls. For this purpose in FIG. 3G there is illustrated the instrument systems 150A and 160A. Usually the instrument system 150A is flexible as it has to conform to the shape and contour of the inside of the vessel or lumen. The instrument systems 150A and 160A carry respective end effectors 150 and 160. These may be the same type end effectors described in connection with FIGS. 3C and 3D. FIG. 3G shows the stitching being completed at 175 at one end of the stent 173, and further shows the instrument systems in action at the other end of the stent securing the other end thereof by means of the illustrated instrument systems 150A and 160A.

In FIG. 3G the instrument system 150A may enter the anatomy through a lumen from a natural body orifice, or percutaneously. The instrument system 160A may be positioned at the lumen via an incision at a convenient location proximal to the operative site. The stitching action may be direct surgeon controlled my manipulation at a master station or can be under automatic control. In FIG. 3G the securing may be for a newly placed object or can be used to repair an existing object. For example, the technique explained can be used for AAA stent failures.

Figure 3H:
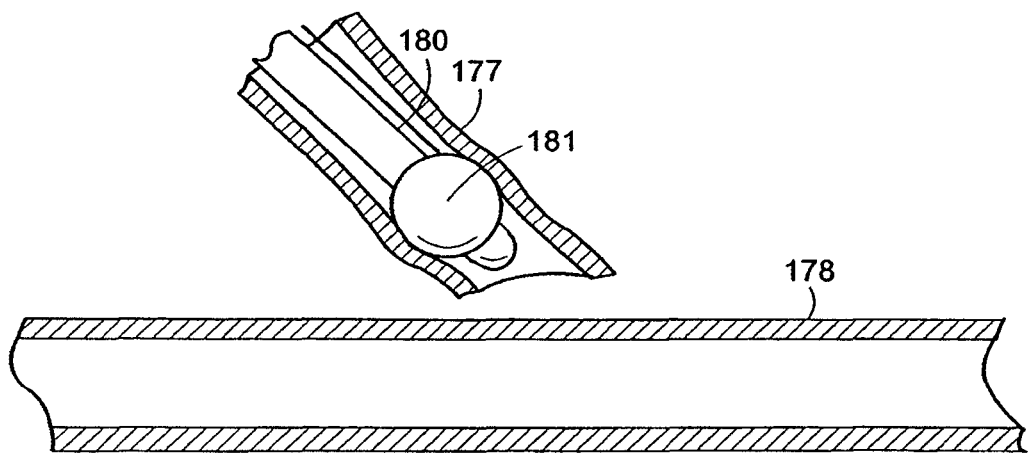
FIG. 3H illustrates a first step in a procedure for attaching one vessel to another such as in bypass surgery.
Figure 3I:
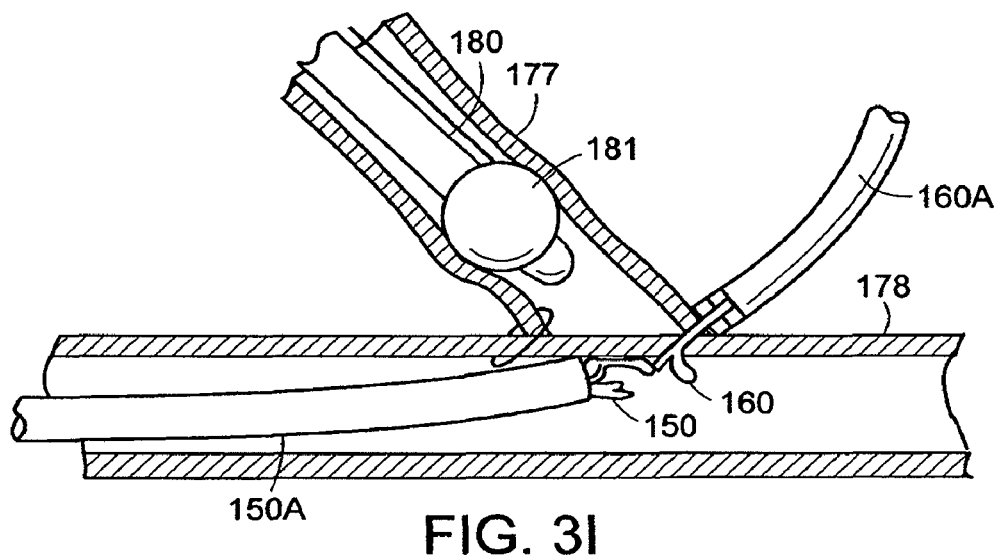
FIG. 3I illustrates a second step in a procedure for attaching one vessel to another.
Figure 3J:
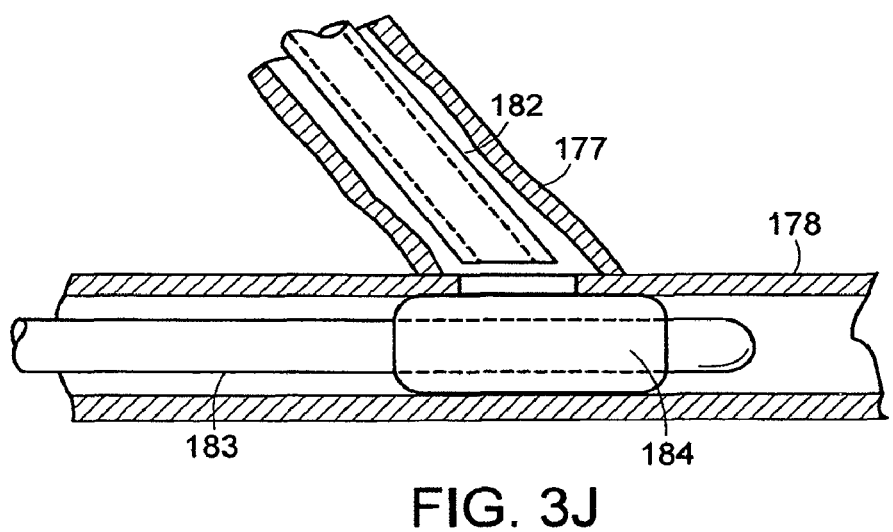
FIG. 3J illustrates a third step in a procedure for attaching one vessel to another.

Refer now to FIGS. 3H through 3J for an illustration of another surgical procedure that can be performed using the present inventive techniques. This example relates to the attachment of one vessel or lumen 177 to another vessel or lumen 178. This is a technique that can be used, for example, in performing a cardiac by-pass. In the illustrated steps the same instrument systems may be employed as previously discussed in connection with earlier embodiments that are described herein. This may include both flexible and rigid systems. Furthermore it is noted in this particular procedure that more than two instrument systems are employed. For example, refer to FIG. 3I where three instrument systems are shown, two positioned within respective lumens and one positioned outside the lumens.

FIG. 3H shows the lumen or vessel 178 to which the vessel or lumen 177 is to be attached. This illustrates the first step in the procedure of positioning the lumen 177 by means of the instrument system 180 that is disposed within the lumen 177.

The instrument system 180 may carry a balloon 181 for example, that is inflated to hold the lumen 177 in place. The instrument system 180 may then be advanced to position the lumen 177 toward the position illustrated in FIG. 3I. The control of movement of the instrument system 180 may be by means of surgeon control from a master station input device. In this procedure, as well as other procedures described herein a viewing endoscope is used to assist in the positioning of instrument systems.

FIG. 3I now shows the next step in the procedure of attaching the tapered end of the vessel 177 to the side wall of the vessel 178. For this purpose there is provided the previously described instrument systems 150A and 160A. These instrument systems are used to sew or suture about the open end of the vessel 177 to attach it to the side wall of the vessel 178. This sewing or suturing step is performed with the use and control of the end effectors 150 and 160. In FIG. 3I it is noted that the instrument system 180 may be kept in place during this step to hold the vessel or lumen 177 against the vessel or lumen 178 to assure accurate attachment. At least parts of the procedures may be performed automatically, particularly the sewing or suturing technique.

After the step illustrated in FIG. 3I is completed then an opening is to be cut in the sidewall of lumen 178 to allow fluid flow between lumens. This is illustrated in FIG. 3J where additional instrument systems are now employed. One instrument system 182 may carry a cutting blade to perform the opening of the sidewall in the lumen 178. In the other lumen 178 there is disposed the instrument system 183 that carries a balloon 184 that is meant to hold the sidewall in place as the cutting operation is performed. For the purpose of illustration only one balloon id shown in FIG. 3J, however, instead a pair of balloons may be used, one positioned on either side of the opening so that there is no interference between the cutting instrument and the supporting balloons.

Figure 3K:
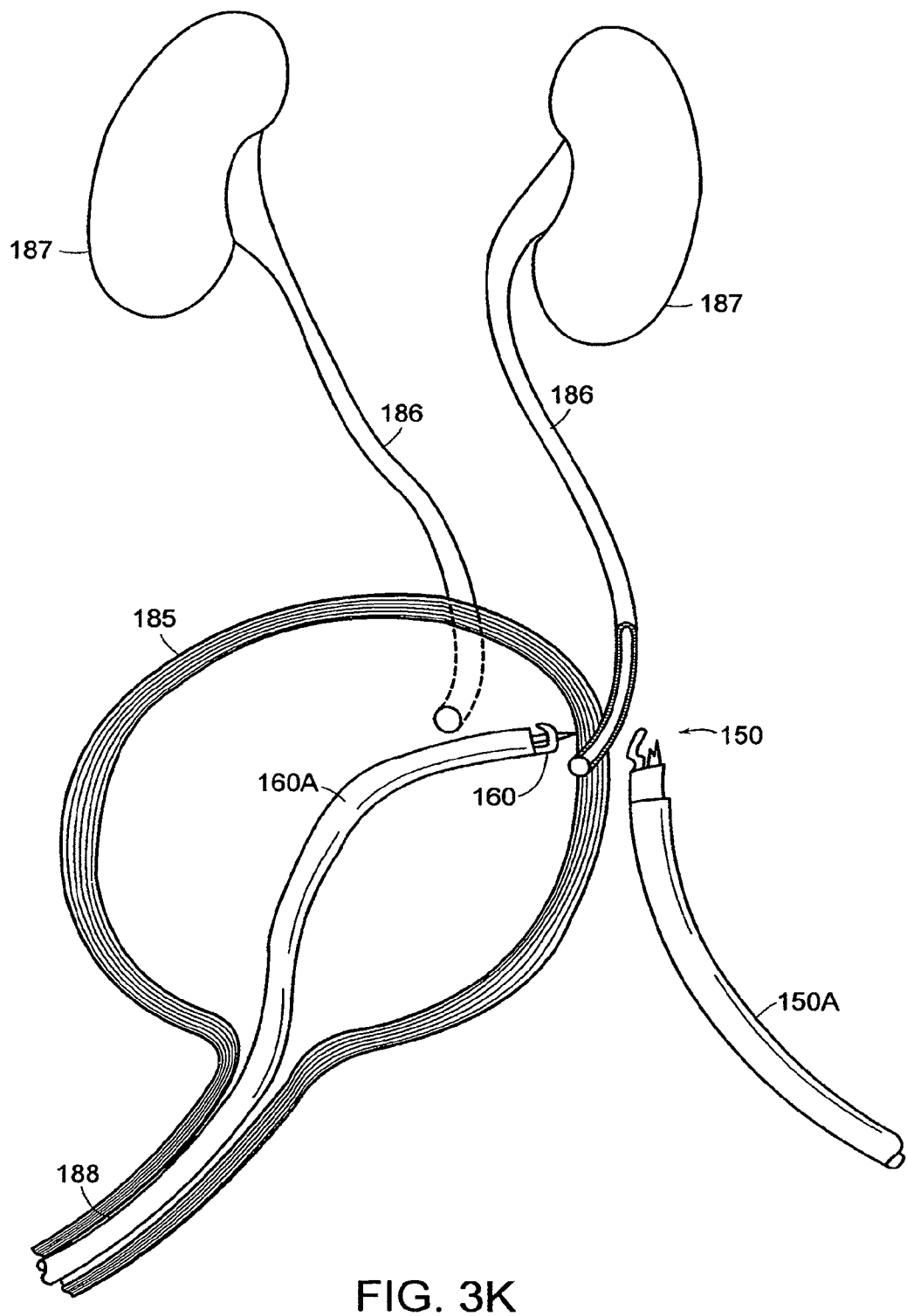
FIG. 3K shows the use of dual instruments in a bladder procedure.

Refer now to another use of the concepts of the invention illustrated in FIG. 3K.

This illustrates a surgical procedure that is performed in the bladder 185. FIG. 3K shows one instrument system 160A passing through the urethra 188 into the interior of the bladder. This is the instrument system 160A carrying the needle end effector 160. FIG. 3K also illustrates the other instrument system 150A carrying the hooked end effector 150. Both of these instrument systems are shown in relative proximity to each other and can be used to perform any one of a number of different procedures. For example, the instrument systems may be used to close the sphincter at the base of the ureter tube 186 that couples to the kidney 187.

Figure 3L:
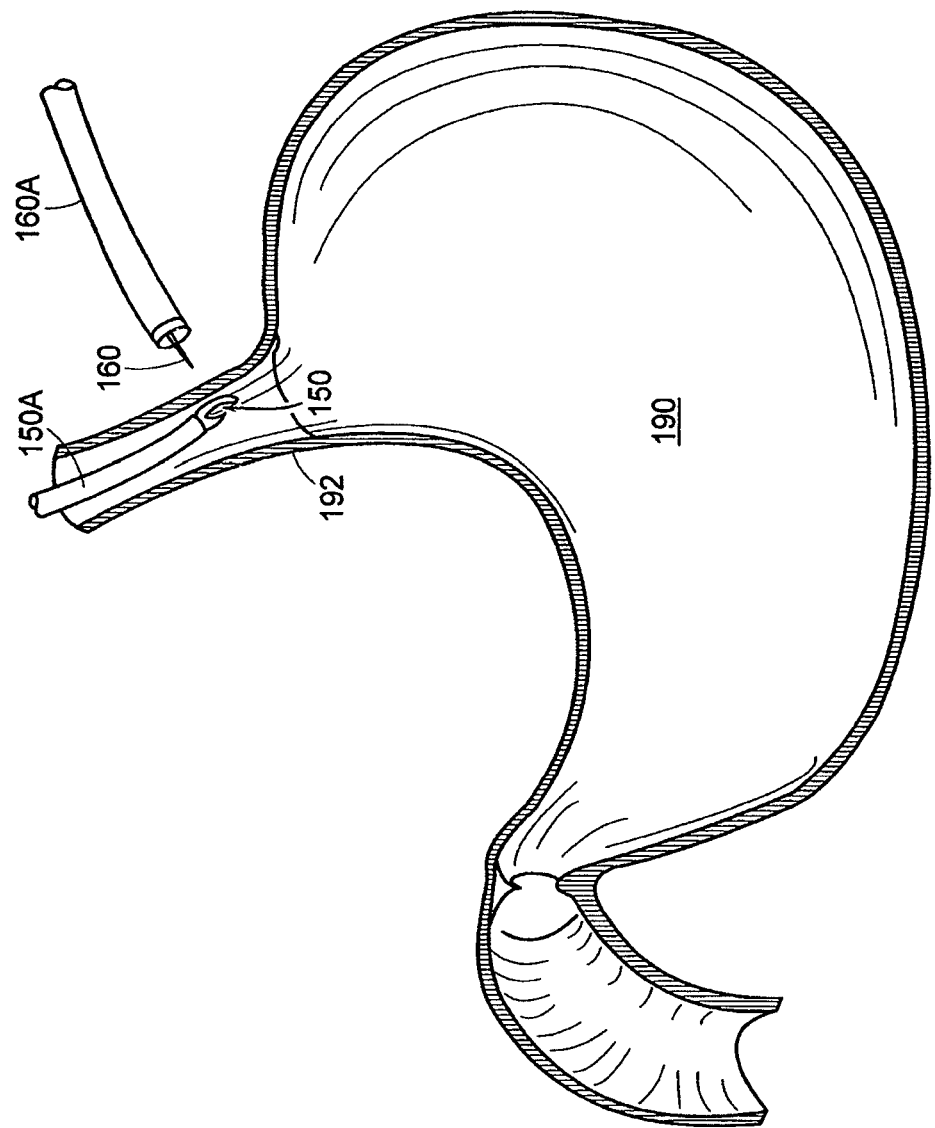
FIG. 3L illustrates the use of dual instruments in a stomach procedure.

FIG. 3L is a further illustration of the use of the instrument systems of the invention in closing the sphincter leading into the stomach 190 at the gastro-esophageol juncture. This is a procedure that is useable to reduce acid reflux that can occur in some patients. By reducing the size of the port at that point acids from the stomach are impeded from backing up into the esophagus. Thus, in FIG. 3L the aforementioned instrument systems 150A and 160A are used to perform a sewing or suturing operation so as to constrict the sphincter at the area 192 illustrated in FIG. 3L. The instrument system 150A carries the hook end effector 150 while the instrument system 160A carries the needle end effector 160. Both the instrument systems may be operated in the same manner as described previously in connection with other procedures that have been described herein.

Figure 5:
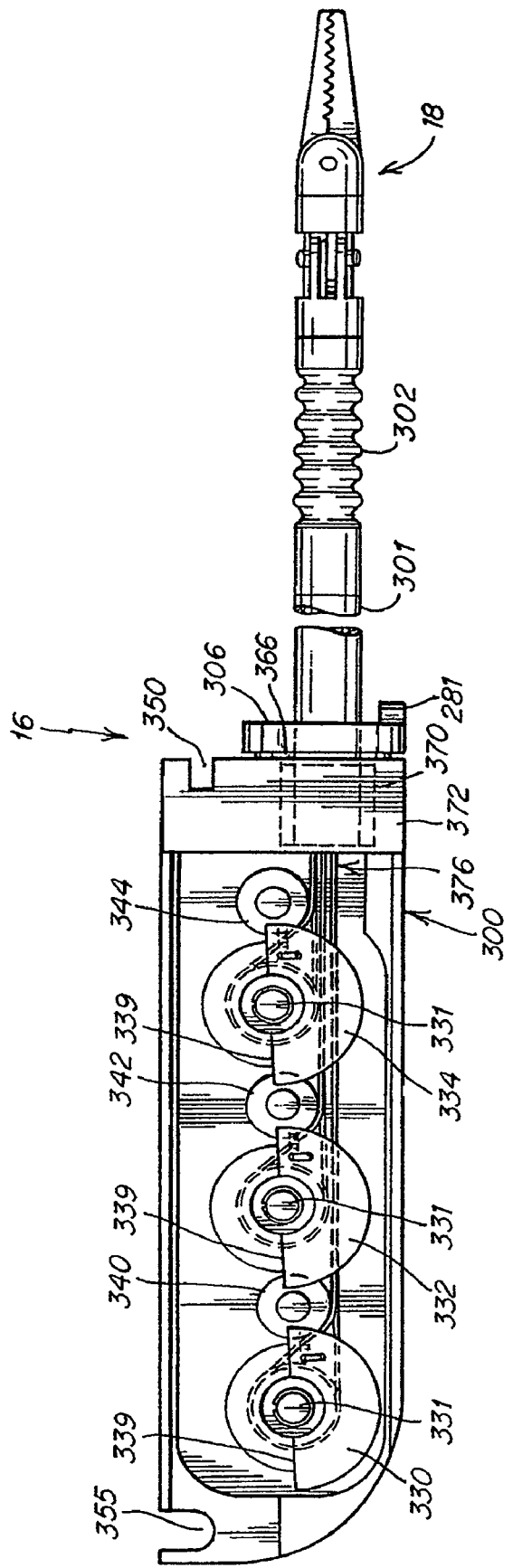
FIG. 5 is a top plan view of the instrument insert itself.

FIG. 4 is an exploded perspective view of another version of the cable drive mechanism and tool. FIG. 5 is a top plan view of the rigid instrument insert itself. FIG. 4 is an exploded perspective view of the cable drive mechanism and instrument illustrating the de-coupling concepts at the slave station S. A section of the surgical tabletop T which supports the rigid post 19 is shown. The drive unit 8 is supported from the side of the tabletop by an L-shaped brace 210 that carries an attaching member 212. The brace 210 is suitably secured to the table T. The drive unit 8 is secured to the attaching member 212 by means of a clamp 214. Similarly, the rigid support rod 19 is secured to the attaching member 212 by means of another clamping mechanism 216.

Also in FIG. 4 the instrument 14 is shown detached from (or not yet attached to) support post 19 at bracket 25. The instrument 14 along with cables 21 and 22 and lightweight housing section 856 provide a relatively small and lightweight decoupleable slave unit that is readily manually engageable (insertable) into the patient at the guide tube 24.

After insertion, the instrument assembly, with attached cables 21, 22 and housing 856, is attached to the support post 19 by means of the knob 26 engaging a threaded hole in base 452 of adapter 15. At the other end of the support post 19, bracket 216 has a knob 213 that is tightened when the support rod 19 is in the desired position. The support rod 19, at its vertical arm 19A, essentially moves up and down through the clamp 216. Similarly, the mounting bracket 25 can move along the horizontal arm 19B of the support rod to be secured at different positions therealong. A further clamp 214 supports and enables the drive unit 8 to be moved to different positions along the attaching member 212. FIG. 4 also shows the coupler 230 which is pivotally coupled from base piece 234 by means of the pivot pin 232. The coupler 230 is for engaging with and supporting the proximal end of the instrument insert 16.

The first housing section 855 also carries oppositely disposed thumb screws 875 (see FIG. 4). These may be threaded through flanges 876. When loosened, these set screws enable the second housing section 856 to engage with the first housing section 855. For this purpose, there is provided a slot 878 illustrated in FIG. 4. Once the second housing section 856 is engaged with the first housing section 855, then the thumb screws 875 may be tightened to hold the two housing sections together, at the same time facilitating engagement between the coupler disks 862 and the coupler spindles 860.

As illustrated in FIG. 4, the two housing sections 855 and 856 are separable from each other so that the relatively compact slave unit can be engaged and disengaged from the motor array, particularly from the first housing section 855 that contains the motors 800. The first housing section 855, as described previously, contains the motors 800 and their corresponding coupler disks 862. In FIG. 4, the second housing section 856 primarily accommodates and supports the coupler spindles 860 and the cabling extending from each of the spindles to the cable bundles 21 and 22 depicted in FIG. 4.

FIG. 4 also shows details of the adaptor including the carriage 226 supported on rails 224. The carriage 226 holds the base piece 234 that, in turn, supports the instrument insert. The coupler 230 of the adaptor provides mechanical drive to the instrument insert. The carriage and rails are pivoted at 225 to provide one degree of freedom, while the in and out motion of the carriage provides another degree of freedom to the instrument.

As shown in FIG. 5, each wheel of the instrument coupler 300 has two cables 376 that are affixed to the wheel and wrapped about opposite sides at its base. The lower cable rides over one of the idler pulleys or capstans (e.g., capstan 34), which routes the cables toward the center of the instrument stem 301. It is desirable to maintain the cables near the center of the instrument stem. The closer the cables are to the central axis of the stem, the less disturbance motion on the cables when the insert stem is rotated. The cables may then be routed through fixed-length plastic tubes that are affixed to the proximal end of the stem section 301 and the distal end of the stem section 302. The tubes maintain constant length pathways for the cables as they move within the instrument stem.

The instrument coupler 300 is also provided with a registration slot 350 at its distal end. The slot 350 engages with a registration pin 352 supported between the bars 270 and 272 of base piece 234. The coupler 300 is also provided with a clamping slot 355 on its proximal end for accommodating the threaded portion of the clamping knob 327 (on adapter coupler 230). The knob 327 affirmatively engages and interconnects the couplers 230 and 300.

In operation, once the surgeon has selected a particular instrument insert 16, it is inserted into the adapter 15. The proximal stem 301, having the distal stem 302 and the tool 18 at the distal end, extend through the adapter guide tube 24. FIG. 4 shows the tool 18 extending out of the guide tube 24 when the surgical instrument 16 is fully inserted into the adaptor 15. When it is fully inserted, the tab 281 on the axial wheel 306 engages with the mating detent 280 in pulley 279. Also, the registration slot 350 engages with the registration pin 352. Then the coupler 230 is pivoted over the base 300 of the instrument insert 16. As this pivoting occurs, the respective wheels of the coupler 230 and the coupler 300 interengage so that drive can occur from the coupler 230 to the insert 16. The knob 327 is secured down so that the two couplers 230 and 300 remain in fixed relative positions.

FIG. 6 is a perspective view of one embodiment of the flexible instrument system 500 illustrated in FIG. 1. FIG. 7 is an enlarged detailed perspective view of the end effector that may be used with the flexible instrument system. FIG. 1 depicts flexible instrument system 500 supported from support bracket 502, which extends to the operating table. Usually the support bracket is supported from the side of the operating table and may be adjustable in position relative to the operating table, to dispose system 500 in a convenient position over or relative to the patient. In one embodiment, bracket 502 is secured to the operating table at one end. The other end of bracket 502 supports the entire flexible instrument by means of a two-piece structure similar to that described in copending U.S. Provisional Application Ser. No. 60/279,087 filed Mar. 27, 2001 the entire teachings of which are concorporated herein by reference. A knob may be provided on support base 504, not shown in FIG. 1. Once the support base 504 is fixed to the support bracket 502, then the flexible instrument system is maintained in a fixed position at base 504, providing a stable and steady structure during the medical procedure. Like the rigid system in FIG. 1, system 500 can be positioned at an acute angle with respect to the operating table or can be arranged at other convenient positions depending upon the surgical procedure being performed.

Flexible instrument system 500 illustrated in FIG. 6 comprises flexible instrument 510 having a shaft 528 extending to mechanically drivable mechanism 526, which interlocks with base (or receiver) 506. Base 506 is supported on carriage 508. Carriage 508, in turn, is adapted for linear translation and supported by elongated rails 512 and 514. Rails 512 and 514 terminate at one end via end piece 516 which provides further support. Support base 504 terminates rails 512 and 514 at their other end. Carriage 508 includes bearings or bushings 509 that support the carriage from rails 512 and 514.

Flexible instrument system 500 employs two separate cable bundles for mechanically driving the flexible instrument along rails 512 and 514. Pulley 521 (dotted outline), residing within carriage control module 520, receives a first pair of cables 518. Pulley 521 also receives a second set of cables, which runs through carriage 508 to a further pulley 522 supported by end piece 516. The second set of cables controls the translational motion of carriage 508 and terminates at point 519.

FIG. 6 also shows a set of cables 524 for driving control elements, e.g. pulleys within receiver 506. These control elements move the shaft and the tool in several degrees-of-freedom. Arrow J1 indicates the linear translation via module 520. Rotational arrow J2 indicates rotation of flexible shaft 528 of flexible instrument 510 about the inner axis parallel with the shaft length. Arrow J3 represents the flexing or bending of flexible shaft 528 at controlled flexible segment 530. In this embodiment, flexible segment 530 is positioned directly adjacent tool 534 at the distal end of shaft 528. Arrow J4 represents the pivot action of a wrist joint, which links tool 534 to shaft 528, about axis 532. In this embodiment, tool 534 is exemplified as a grasper, and arrows J5 and J6 represent the opening and closing actions of the tool jaws. Motions indicated by arrows J2-J6 are controlled from cabling 524 originating at receiver 506.

FIG. 7 provides an enlarged perspective view of the distal end of shaft 528 including flexible segment 530 and tool 534. The segment 530 corresponds to the section 500B illustrated in FIG. 3, while the end effector 534 corresponds to the end effector 500A illustrated in FIG. 3. Tool 534 comprises upper grip or jaw 602 and lower grip or jaw 603, both supported from link 601. Base 600 is affixed to or integral with flexible shaft 528. Link 601 is rotatably connected to base 600 about axis 532. A pivot pin may be provided for this connection. Upper and lower jaws 602 and 603 are rotatably connected to link 601 about axis 536 and again, a pivot pin can provide this connection.

FIG. 7 shows eight cables at 538 extending through the hollow inside of shaft 528 for control of tool 534 and flexible segment 530. Two of these cables operate the bend of flexible segment 530, two cables operate one of the jaws 602, two cables operate the other of the jaws 603 and the last two cables operate the wrist action about the axis 532. All of these cables travel through the hollow shaft 528 and through appropriate holes in flexible segment 530 e.g. wire 525, as well as holes in base 600. Each of these pairs of cables operates in concert to open and close jaws, pivot about the wrist, and bend flexible segment 530.

One pair of cables travels through shaft 528 and through appropriate holes in the base 600, wrapping around a curved surface of the link 601 and then attaching to the link. Tension on this pair of cables rotates the link 601 along with the upper and lower grips or jaws 602 and 603 about axis 532.

Two other pairs of cables also extend through the shaft 528 and through holes in the base and then pass between fixed posts 612. These posts constrain the cables to pass substantially through axis 532, which defines rotation of link 601. This construction essentially allows free rotation of link 601 with minimal length changes in the cables passing to jaws 602 and 603. Thus, the cables actuating jaws 602 and 603 are essentially decoupled from the motion of link 601 and are not effected by any rotation of link 601. Cables controlling jaw movement terminate on jaws 602 and 603. These cables permit independent operation of the jaws 602 and 603 in respective clockwise and counter clockwise directions with respect to axis 536. A similar set of cables is present on the under-side of the link 601 (not shown). Each of the jaws 602 and 603, as well as the link 601, may be constructed of metal. Alternatively, link 601 may be constructed of a hard plastic material.

Base 600 may also be constructed of a plastic material and may be integral with shaft 528.

Bending of flexible segment 530 is provided via diametrically disposed slots 662, which define spaced ribs 664. Flexible segment 530 also has a longitudinally extending wall 665 through which cabling may extend, particularly for the operation of the tool. One of the pairs of cables of bundle 538 controlling flexible segment 530 terminates where base 600 intercouples with shaft 528. This pair of cables works in concert to cause bending as indicated by arrow J3, i.e. in a direction orthogonal to the pivoting provided at wrist axis 532. The flexible segment 530 may also be provided with additional degrees of freedom by controlling bending in two axes, direction J3 that is illustrated and a direction orthogonal thereto.

Figure 8:
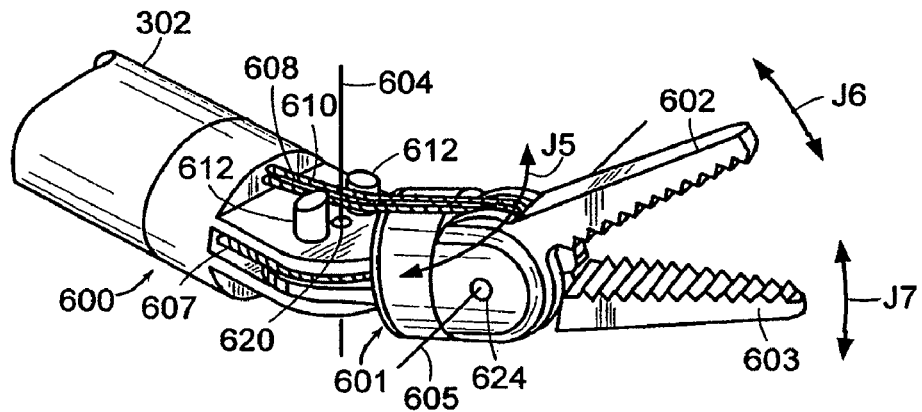
FIG. 8 is a perspective view at the tool.
Figure 9:
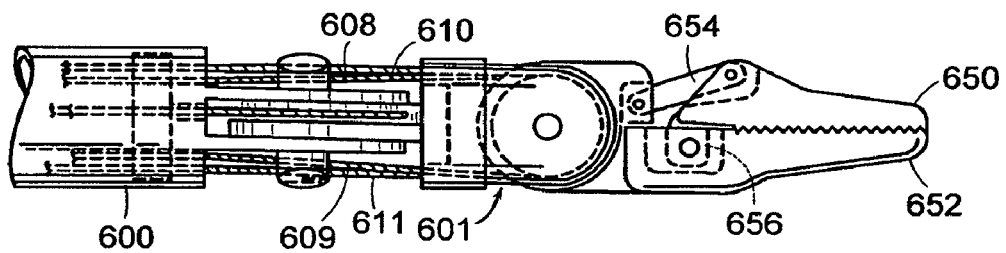
FIG. 9 is a side elevation view of the needle driver.
Figure 10:
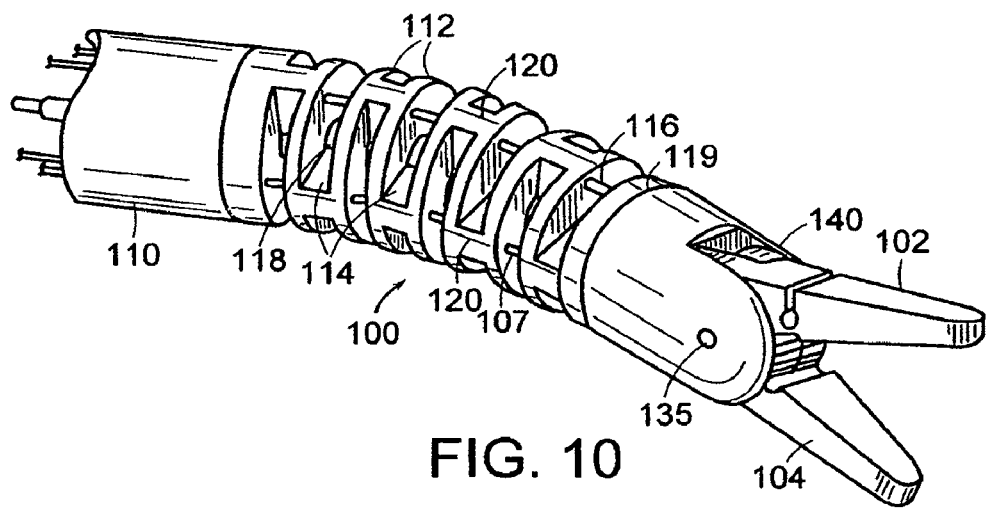
FIG. 10 is a perspective view of an embodiment of a flexible or bendable wrist just proximal to the tool.

FIGS. 8, 9 and 10 show different embodiments that can be used with either instrument but that are illustrated, in particular, for the rigid instrument system. FIG. 8 illustrates the construction of one form of a tool. FIG. 8 is a perspective view. The tool 18 is comprised of four members including a base 600, link 601, upper grip or jaw 602 and lower grip or jaw 603. The base 600 is affixed to the flexible stem section 302 (see FIG. 5). The flexible stem may be constructed of a ribbed plastic. This flexible section is used so that the instrument will readily bend through the curved part of the guide tube 24.

The link 601 is rotatably connected to the base 600 about axis 604. FIG. 8 illustrates a pivot pin 620 at axis 604. The upper and lower jaws 602 and 603 are rotatably connected by pivot pin 624 to the link 601 about axis 605, where axis 605 is essentially perpendicular to axis 604.

Six cables 606-611 actuate the four members 600-603 of the tool. Cable 606 travels through the insert stem (section 302) and through a hole in the base 600, wraps around curved surface 626 on link 601, and then attaches on link 601 at 630. Tension on cable 606 rotates the link 601, and attached upper and lower grips 602 and 603, about axis 604. Cable 607 provides the opposing action to cable 606, and goes through the same routing pathway, but on the opposite sides of the insert. Cable 607 may also attach to link 601 generally at 630.

Cables 608 and 610 also travel through the stem 301, 302 and though holes in the base 600. The cables 608 and 610 then pass between two fixed posts 612. These posts constrain the cables to pass substantially through the axis 604, which defines rotation of the link 601. This construction essentially allows free rotation of the link 601 with minimal length changes in cables 608-611. In other words, the cables 608-611, which actuate the jaws 602 and 603, are essentially decoupled from the motion of link 601. Cables 608 and 610 pass over rounded sections and terminate on jaws 602 and 603, respectively. Tension on cables 608 and 610 rotate jaws 602 and 603 counter-clockwise about axis 605. Finally, as shown in FIG. 8, the cables 609 and 611 pass through the same routing pathway as cables 608 and 610, but on the opposite side of the instrument. These cables 609 and 611 provide the clockwise motion to jaws 602 and 603, respectively. At the jaws 602 and 603, as depicted in FIG. 8, the ends of cables 608-611 may be secured at 635, for example by the use of an adhesive such as epoxy glue, or the cables could be crimped to the jaws.

Reference is now made to FIG. 9. FIG. 9 is a side elevation view of a needle driver version of end effector. This embodiment employs an over-center camming arrangement so that the jaw is not only closed, but is done so at a forced closure.

In FIG. 9, similar reference characters are employed with respect to the embodiment of FIG. 8. Thus, there is provided a base 600, a link 601, an upper jaw 650 and a lower jaw 652. The base 600 is affixed to the flexible stem section 302. Cabling 608-611 operate the end jaws. Linkages 654 and 656 provide the over-center camming operation. The two embodiments of FIGS. 8 and 9 employ a fixed wrist pivot. An alternate construction is illustrated in FIG. 10 in which there is provided, in place of a wrist pivot, a flexible or bending section. This type of bendable section may be used with either flexible or rigid instrument systems.

FIG. 10 is a perspective view of an embodiment of a flexible or bendable wrist just proximal to the tool. FIG. 10 illustrates the manner in which the previously disclosed tools may be used with a flexible or bendable segment of the instrument shaft, whether used with a rigid shaft body or a flexible shaft body or combinations thereof. One of the advantages is that only a single cable needs to be coupled to the tool for actuation thereof. The pitch and yaw of the tool is controlled at the flexible section 100 shown in FIG. 10. This arrangement also lends itself to making the tool disposable or at the very least detachable from the instrument body such as for substitution of another tool. Because the construction becomes more simplified at the tip of the instrument, it makes it possible to construct a tool that is readily detachable from the instrument.

In FIG. 10 there is disclosed one embodiment of a tool, illustrated in conjunction with a flexible shaft or tube having a remotely controllable bending or flexing section 100. The medical instrument may comprise an elongated shaft, such as shaft section 110, having proximal and distal ends; and a tool, such as graspers 102 and 104, supported from the distal end of the elongated shaft and useable in performing a medical procedure on a subject. The tool is actuated preferably by a single tendon or cable that extends through the flexible section 100. In order to provide the pitch and yaw action at the tool, the bending or flexing section 100 is constructed so as to have orthogonal bending by using four cables separated at 90.degree. intervals and by using a center support with ribs and slots about the entire periphery. Refer to the ribs 112 that define corresponding slots 114. The ribs define at each of their centers a center support passage 118 that has extending therethrough the cable 136. The bending section 100 is at the end of tube section 110. The section 110 may be flexible itself, may be smooth as shown, or may be fluted.

The bending section 100 has alternating ridges 120 to provide universal bending. This version enables bending in orthogonal directions by means of four cables 106, 107, 116 and 117. The operation of cables 106 and 107 provides flexing in one degree-of-freedom while an added orthogonal degree-of-freedom is provided by operation of cables 116 and 117. Each of the cables 106, 107, 116, and 117 have at their terminating ends respective balls 106A, 107A, 116A, and 117A that may be held in corresponding recesses in a distal end wall 119 of the flexible section 100.

The bending section 100, as indicated previously, includes a series of spaced ribs 112 disposed, in parallel, with the plane of each rib extending orthogonal to the longitudinal axis of the section 100. At the proximal end of the bendable section an end rib connects to the shaft section 110, while at the distal end there is provided the distal end wall 119 that supports the ends of the cables. Each of the ribs 112 are held in spaced relationship by means of the alternating ridges 120. As depicted in FIG. 10 these ribs are identified as horizontal ribs 120A, alternating with vertical ribs 120B. This structure has been found to provide excellent support at the center passage for the actuating cable 136, while also providing enhanced flexibility in orthogonal directions of bending or flexing.

The grippers 102 and 104 are supported for opening and closing by means of a pivot pin 135 that extends along a pivot axis. These grippers may be supported in link 140. Refer to the exploded perspective view of FIG. 10 showing the pin 135, and grippers 102 and 104. The pin 135 may be supported at its ends in opposite sides of link 140.

Figure 11:
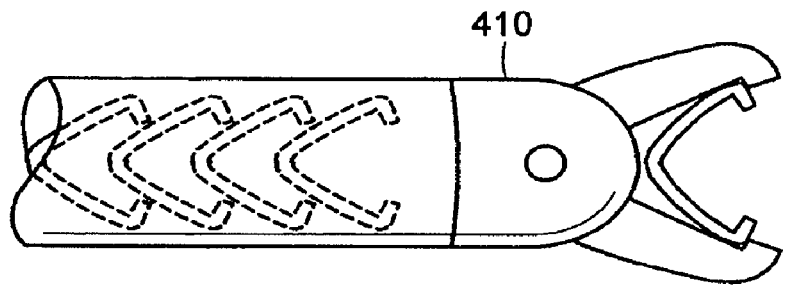
FIGS. 11-14 illustrate different end effector constructions that may be used with either flexible or rigid instruments.
Figure 12:
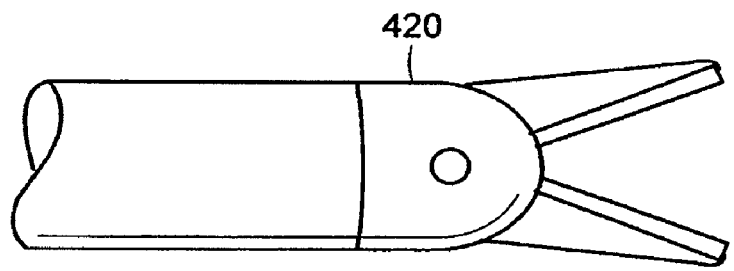
Figure 13:
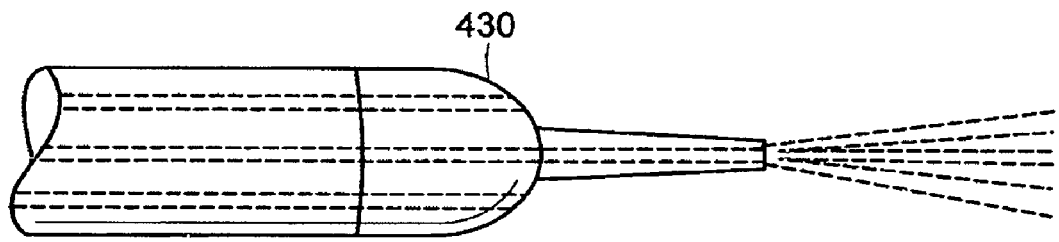
Figure 14:
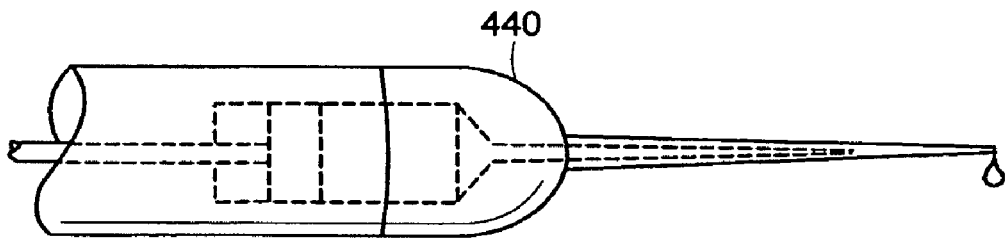

Reference is now made to FIGS. 11-14 for an illustration of different end effector devices that can be used with the instrument systems described herein. FIG. 11 shows a clip applier 410. FIG. 12 shows a cutting jaw 420. FIG. 13 shows a device 430 for applying a solution or agent to an operative site. FIG. 14 shows a syringe type device 440 useable as an end effector.

The surgical robotic system, as illustrated in FIGS. 15-17, although preferably used to perform minimally invasive surgery, may also be used to perform other procedures as well, such as open or endoscopic surgical procedure. FIG. 15 is a perspective view at the slave station of the system of FIG. 1 illustrating the interchangeable instrument concepts as applied in a dual instrument system. FIG. 16 is a cross-sectional view through the storage chamber and as taken along line 16-16 of FIG. 15. FIG. 17 is a longitudinal cross-sectional view, as taken along line 17-17 of FIG. 15, and showing both a stored articulating instrument and a stored fluid dispensing.

Reference is now made to FIG. 15 which is a perspective view illustrating the instrument 14 and the adaptor 15 at the slave station S. This instrument system is secured in the manner illustrated in FIG. 1 to the rigid post 502 that supports the surgical instrument by way of a mounting bracket. FIG. 15 also shows several cables that may be separated into five sets for controlling different motions and actions at the slave station. These are individual cables of the aforementioned bundles 21 and 22 referred to in FIG. 4. FIG. 15 also illustrates the support yoke 220 that is secured to the mounting bracket 31, the pivot piece 222, and support rails 224 for the carriage 226. The rails are supported in end pieces 241 and 262 with the end piece 241 attached to the pivot piece 222. The pivot piece 222 pivots relative to the support yoke 220 about pivot pin 225. A base piece 234 is supported under the carriage 226 by means of the support post 228. The support post 228 in essence supports the entire instrument assembly, including the adaptor 15 and the instrument 14.

As indicated previously, the support yoke 220 is supported in a fixed position from the mounting bracket 31. The support yoke 220 may be considered as having an upper leg 236 and a lower leg 238. In the opening 239 between these legs 236 and 238 is arranged the pivot piece 222. Cabling extends into the support yoke 220. This is illustrated in FIG. 15 by the cable set 501. Associated with the pivot piece 222 and the carriage 226 are pulleys (not shown) that receive the cabling for control of two degrees-of-freedom. This control from the cable set 501 includes pivoting of the entire instrument assembly about the pivot pin 225. This action pivots the guide tube 24 essentially in a single plane. This pivoting is preferably about an incision of the patient which is placed directly under, and in line with, the pivot pin 225. Other cables of set 501 control the carriage 226 in a linear path in the direction of the arrow 227. See also the cables 229 extending between the carriage 226 and the end pieces 241 and 262. The carriage moves the instrument and guide tube 24 back and forth in the direction of the operative site OS. Incidentally, in FIG. 15 the instrument is in its fully advanced state with the tool at the operative site OS.

The base piece 234 is the main support for the interchangeable instrument apparatus of the invention. The base piece 234 supports the guide tube 24, the instrument storage chamber 540, and the instrument driver 550. The instrument driver 550 is supported from another carriage, depicted in FIGS. 15 and 17 as the carriage 552, and that, in turn, is supported for translation on the carriage rails 554. The rails 554 are supported at opposite ends at end pieces 556 and 558, in a manner similar to the support for the other carriage 226. A support post 560 interconnects the carriage 552 with the instrument driver housing 570.

With further reference to FIG. 15, and as mentioned previously, there are a number of cable sets from bundles 21 and 22 coupled to and for controlling certain actions of the instrument system. Mention has been made of the cable set 501 for controlling instrument pivoting and translation, as previously explained. In addition, FIG. 15 depicts four other cable sets 503, 505, 507, and 509. Cable set 503 controls rotation of the guide tube 24. Cable set 505 controls the carriage 552, and, in turn, the extending and retracting of the instrument driver for instrument exchange. Cable set 507 controls rotation of the instrument through rotation of the instrument driver. Finally, cable set 509 controls the tool via the instrument driver and instrument. There is also one other set of control cables not specifically illustrated in FIG. 15 that controls the indexing motor 565, to be discussed in further detail later.

FIG. 17 shows a cross-sectional view through the interchangeable instrument portion of the overall instrument system. This clearly illustrates the internal cable and pulley arrangement for the various motion controls. There is a pulley 301 driven from the cable set 503 that controls rotation of the guide tube 24. There is also a pulley 303 driven from cable set 505, along with a companion pulley 305 that provides control for the carriage 552. FIG. 17 also illustrates another pulley 307 driven from cable set 507, and for controlling the rotation of the instrument driver 550, and, in turn, the selected instrument.

FIG. 17 illustrates the guide tube 24 supported from the base piece 234. The guide tube 24 is hollow, has a curved distal end as illustrated in FIG. 15, and is adapted to receive the individual instruments or work sections 541 (articulating) or 590 (fluid-filled) disposed in the instrument storage chamber 540, as well as the instrument driver 550. Refer to FIG. 17 for an illustration of the instrument and instrument driver positioned in the guide tube 24. FIG. 17 shows the instrument driver 550 in its rest or disengaged position. The proximal end 24A of the guide tube 24 is supported in the base piece 234 by means of a pair of bearings 235 so that the guide tube 24 is free to rotate in the base piece 234. This rotation is controlled from the pulley 237 which is secured to the outer surface of the guide tube 24 by means of a set screw 231. The pulley 237 is controlled to rotate by means of the cabling 310 that intercouples the pulleys 301 and 237 and that is an extension of the cabling 503. Thus, by means of the cable and pulley arrangement, and by means of the rotational support of the guide tube 24, the rotational position of the guide tube 24 is controlled from cable set 503. Of course, this controlled rotation is effected from the master station via the controller 9, as depicted in the system view of FIG. 1, and as a function of the movements made by the surgeon at the user interface 15.

As indicated before the proximal end 24A of the guide tube 24 is supported from the base piece 234. The distal end of the guide tube 24, which is adapted to extend through the patient incision, is disposed at the operative site OS illustrated about the instrument member 20 in FIG. 15, and where a medical or surgical procedure is to be performed. In the system shown in FIG. 15 the distal end of the guide tube 24 is curved at 24B. In this way by rotating the guide tube 24 about its longitudinal axis there is provided a further degree-of-freedom so as to place the distal end of the instrument at any position in three-dimensional space. The rotation of the guide tube 24 enables an orbiting of the instrument end about the axis of the guide tube 24. The guide tube 24 is preferably rigid and constructed of a metal such as aluminum.

FIG. 17 also illustrates a cross-section of the instrument storage chamber 540 including the storage magazine 549, and showing two of the six instrument passages 542 in the storage magazine 549. The instrument storage chamber may also be referred to herein as an instrument retainer. In FIG. 17 one of the fluid retaining instruments 590 is about to be engaged by the instrument driver 550. The other articulating type instrument 541 is in place (storage or rest position) in the instrument storage chamber 540, and out of the path of the instrument driver 550. The instrument 541 carries a gripper tool, but other instruments may also be carried such as a scissors. Because these instruments are adapted to pass to the guide tube 24 and be positioned at the distal end 24B thereof, the body 548 of each instrument is flexible so as to be able to curve with the curvature of the guide tube 24.

Although reference is made herein to the separate instrument and instrument driver, such as illustrated in FIG. 17, once they are engaged they function as a single piece instrument member. Accordingly reference is also made herein to the instrument driver 550 as a "driver section" of the overall one piece instrument member, and the instrument 541 or 590 as a "working section" of the instrument member. The instrument member has also been previously discussed as having a "coupling section" or "interface section", which is defined between the working section and the driver section where the cables interlock by means of an engaging hook arrangement. This is shown in FIG. 17 at 559.

The carriage 552 illustrated in FIG. 17 is moved linearly by the cables 555 that extend between pulleys 303 and 305. These cables attach to the carriage 552. The carriage movement is controlled from cable set 505. It is the movement of the carriage 552 that drives the instrument driver (driver section) 550. The instrument driver 550, in its rest or disengaged position, is supported between the instrument driver housing 570 and the wall 562 that is used for support of the instrument storage chamber 540. The instrument magazine 549 is rotationally supported by means of the axle or shaft 547, with the use of bushings or bearings, not shown. This support is between walls 562 and 563.

FIG. 17 shows the very distal end 525 of the instrument driver (transporter) 550 supported at wall 562. In the rest position of the instrument driver 550 the driver is out of engagement with the instruments and the magazine 549, thus permitting rotation of the instrument storage chamber 540. The proximal end 526 of the instrument driver 550 is supported at the instrument driver housing 570. It may be rotationally supported by means of a bushing 527. The instrument driver 550 is supported for rotation, but rotation is only enabled once the driver has engaged the instrument and preferably is at the operative site. The rotation of the instrument driver 550 is controlled from cable set 507 by way of the pulley 307.

In FIG. 15 the cable set 509 is illustrated as controlling the instrument motions including tool actuation. These cables control a series of pulleys shown in FIG. 17 as pulleys 529. As indicted in FIG. 17 these pulleys control cabling that extends through the instrument driver and the instrument for control of instrument and tool motions when articulating type tools are selected. The cables that are controlled from these pulleys may control three degrees-of-freedom of the instrument, including pivoting at the wrist and two for gripper action. The same engagement arrangement can be used in this second embodiment of the invention including the mating hook arrangement, interlocked at interface 559 when the instrument driver and instrument are engaged.

In one version of the invention a rotating member may be used for control of actuating rods. In the illustrated embodiment of the invention a different arrangement is used that includes a lead screw type of mechanism. This mechanism 591 is illustrated in FIG. 17 next to the pulleys 529. This mechanism includes a drive nut 593 having an internal threaded passage for receiving the actuating rod 592. The actuating rod 592 also has a threaded outer surface and further includes an elongated slot or keyway 594. An anti-rotation key 595 is fixed in position and is adapted to be received in the keyway 594. This engagement between the key 595 and the actuating rod 592, prevents rotation of the actuating rod 592. However, the threaded engagement between the drive nut 593 and the outer threads of the actuating rod 592 enable linear (screw advance) translation of the actuating rod 592. This linear translation of the actuating rod initiates dispensing from the fluid-filled instrument by actuating the instrument member piston.

The drive nut 593 is journaled to the housing 570, but is free to rotate relative to the housing. A bearing 596 is provided to enable rotation of the drive nut 593 relative to the housing 570. The cable set 511 couples about the drive nut 593 to cause rotation thereof. Because the key 595 is fixed in position, then the actuating rod 592 can only move linearly in the direction of the arrow 597. The linear translation of the actuating rod 592 is transferred, via the driver 550, to the actuating rod of the instrument member. This action is, in turn, transferred to the dispensing piston of the syringe member 590. For further details refer to the pending applications referred to before and incorporated by reference herein.

FIG. 17 shows one fluid-filled instrument 590. The cable control via the cable set 511 can provide precise movement of the actuating rod 592 so that all or any portion of the liquid in the dispensing member can be ejected at the appropriate body site. If less than all the liquid is ejected then the instrument can be returned to the storage magazine in readiness for a subsequent use. By keeping track of the degrees of rotation of the drive nut 593, one can ascertain how much of the liquid has been dispensed and how much remains in the syringe member.

Figure 18:
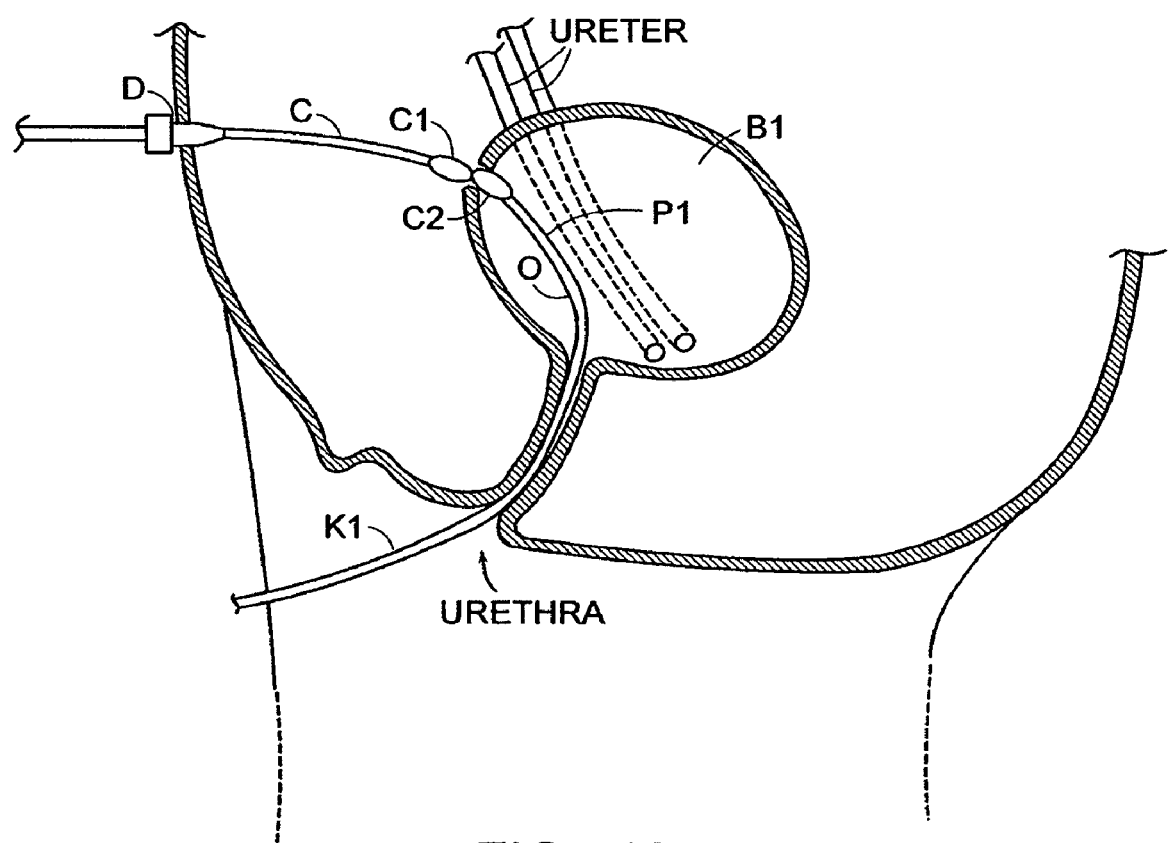
FIG. 18 is schematic diagram of the instrument systems of the present invention as deployed through the urethra for a surgical procedure in the bladder.

FIG. 18 is schematic diagram of the catheter system of the present invention as deployed through the urethra for a surgical procedure in the bladder. FIG. 18 provides a schematic cross-sectional diagram illustrating a surgical procedure where catheter K1 enters a natural body orifice, such as the urethra for carrying out procedures in, for example, the bladder. In FIG. 18 catheter K1 is shown extending into bladder B1. In this example, the computer controlled segment, identified as operative, bendable or flexible segment O in FIG. 18, is positioned at a more proximal section of catheter K1. Bladder B1, being an open cavity, does not have lumens leading from the urethra that would naturally guide a catheter towards any particular operative site. Upon entering bladder B1, catheter K1 can bend in any direction including the direction of the operative site. In this embodiment, because of the more proximal positioning of operative segment O, a surgeon can controllably bend the distal end of catheter K towards the operative site. In the embodiment shown in FIG. 18, the distal end of the catheter, labeled P1, can be rigid or be "passively" flexible, i.e. made of a flexible material and not necessarily controlled for flexure under remote computer control. FIG. 18 also shows another instrument system preferably a rigid instrument system including an instrument C extending through an incision D. The instrument shaft carries an end effector C1 that may be a set of jaws. Similarly, the bendable instrument K1 may carry an end effector C2. These instruments are coordinated in their action so that they can operate together in performing a surgical procedure. Refer also to the previous discussion regarding FIG. 3K.

Figure 19:
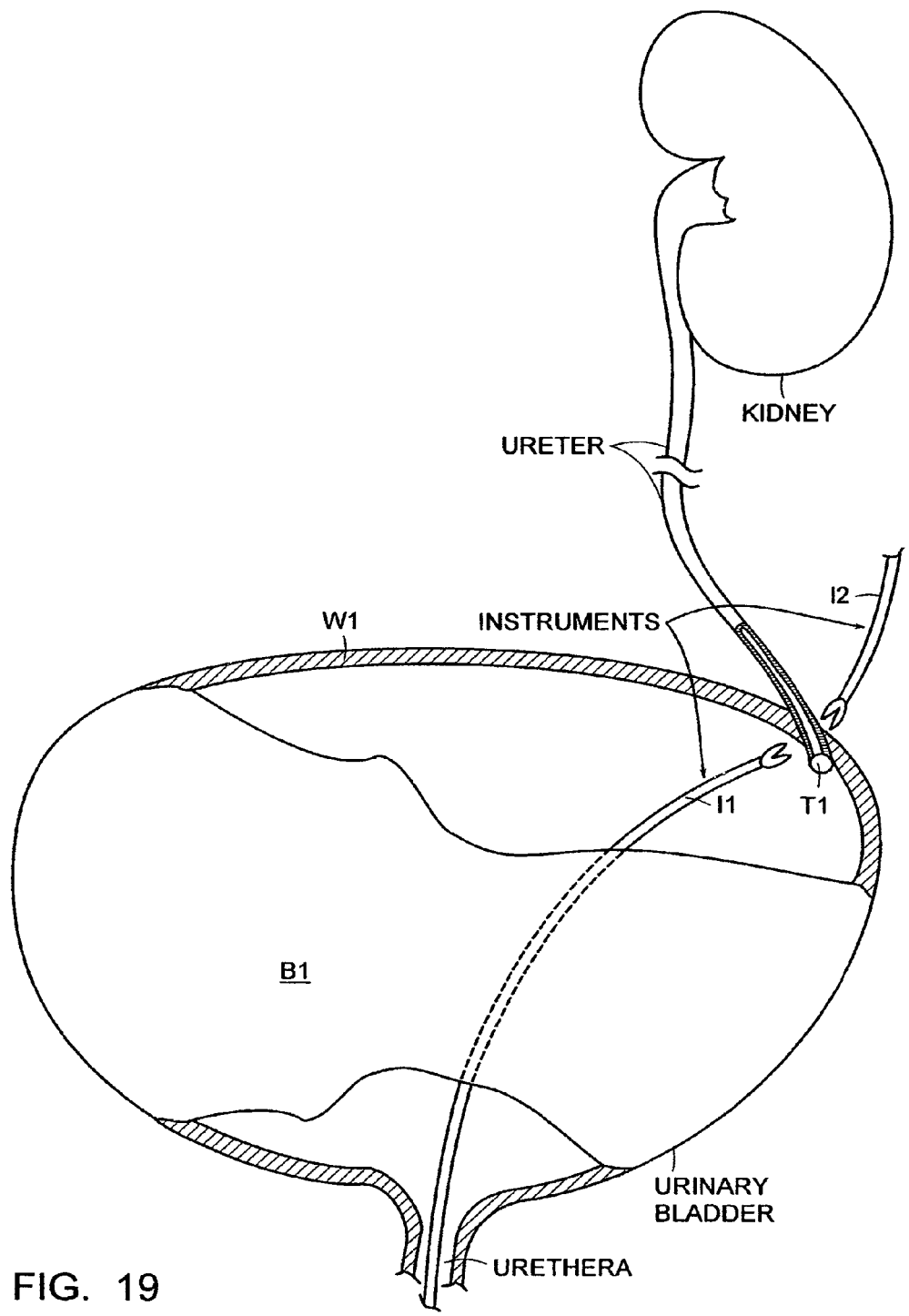
FIG. 19 gives further details of the bladder procedures of FIG. 18.

Refer now to FIG. 19 for added details of the bladder procedure referenced in FIGS. 3K and 18. This drawing also shows the cross-section through the wall WI of the bladder B1, illustrating the ureter tube T1 that extends through the muscle wall to the kidney. This also shows an inside instrument system I1 with a corresponding end effector, as well as an outside instrument system I2 that likewise carries an end effector. These end effectors may be for sewing or for other purposes depending upon the particular procedure that is to be performed. The inside instrument system is usually flexible, while the outside instrument system may be either flexible or rigid.

Reference to a rigid instrument system usually refers to an instrument in which there is a shaft that is primarily rigid and usually meant for insertion into the patient through a small incision such as a laparoscopic incision. However, rigid instruments may also be used to some extent within a natural body orifice. Flexible shaft instruments may be used through a natural body orifice, by percutaneous entry, through an incision or by other means for entry into the patient.

Figure 20:
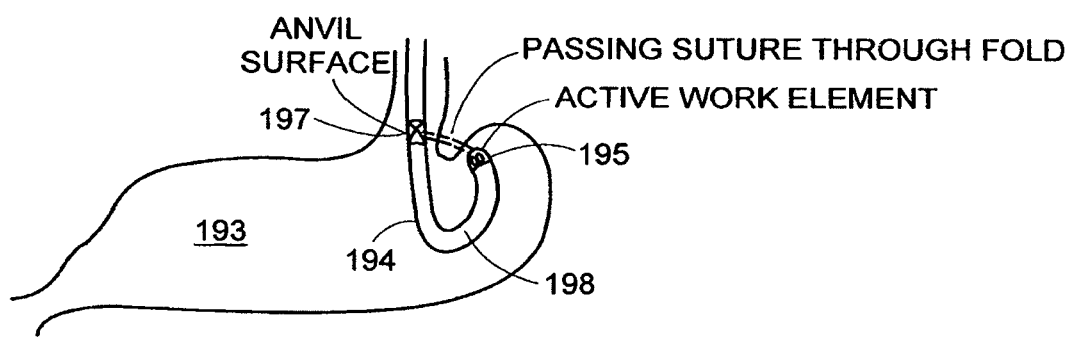
FIG. 20 illustrates still another concept using a single controllable instrument.

FIG. 20 shows still another instrument system that may be used for suturing, sewing or other surgical procedures in a body cavity or vessel such as in the cavity 193 illustrated. The instrument system 194 uses a single instrument arrangement that actually has two or more work areas. By way of example in FIG. 20 there is, at the very distal end of the instrument system 194, an active work element 195. This may be the same as the instrument end effector 160 illustrated in FIG. 3K or may be a set of jaws. In addition to the active work element 195 the instrument system is also provided with an intermediate work element 197. This is another end effector that is adapted to cooperate with the end effector 195 in performing a surgical procedure. For sewing the end effector 197 may be a hook end effector previously described, or it may be an anvil construction. The end effectors shown in FIG. 20 may also be of other types such as, but not limited to, graspers, needle drivers, cauterizing tools, scalpels, etc. The instrument system shown in FIG. 20 is simple in construction using only a single controlled instrument member. Preferably the shaft of the instrument system is curved back upon itself as illustrated at 198 in FIG. 20. This construction enables the one instrument system to be used for performing a complete surgical procedure such as passing a suture through a fold of tissue as illustrated in FIG. 20.

Another concept relates to arthroscopic procedures, but could also apply to other medical procedures. This relates to the use of a single flexible instrument that might be used in, for example, a knee operation through a single entry point, rather than present instrumentation that uses multiple instruments and associated multiple incisions. The procedures described herein are also advantageous in that they can be carried out without requiring open incisions, thus lessening recovery times.

The following are some of the additional features that characterize these inventions and relating to the use of multiple instruments, particularly multiple instruments of different types and adapted for different locations of access to anatomic parts of the body.

(A) The use of instruments intralumenally minimizes the number of incisions that have to be made in a particular procedure.

(B) The intralumenal instrument can be used as a "locator" to assist in locating the extralumenal instrument. For example, one can locate the coronary vessel (often hidden by fat and muscle, and not on the heart surface) for anastomosis by means of the intralumenal instrument.

(C) Provides for multiple instruments in a small space. For example, in bowel anastomosis/resection two instruments may be used intralumenally and one used extralumenally.

(D) Provides for internal and external control of a surgical procedure. For example, in the repair of a failed AAA stent (see FIG. 3G), the intralumenal instrument stabilizes the stent, bringing the loose stent against the vessel wall, while the extralumenal instrument performs an anchoring through the vessel wall.

(E) In all of the above the instruments are preferably computer controllable from a master station with an input device and in coordination with each other. For that purpose the instruments are provided with sensors so each knows the position of the other, and their accurate manipulation can thus be controlled.

(F) The control of operations described herein such as sewing or suturing techniques employs algorithms when operation is substantially totally computer controlled. These algorithms can control such parameters as stitch patterns, stitch tension, stitch spacing, tightness and precision of the stitching.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of performing a medical procedure on a patient, comprising:
   introducing a stent into an anatomical vessel of the patient;
   introducing a first medical instrument and a second medical instrument into the patient, the first medical instrument being located outside of the anatomical vessel, the second medical instrument being located within the anatomical vessel and within an inner space defined by the stent, a distal end of the first medical instrument comprising a first active tool configured to pierce the anatomical vessel and the stent, the second medical instrument comprising a second active tool configured to receive a stitch delivered by the first active tool and extending through the anatomical vessel and the stent;
   conveying control signals from a remote controller to a drive unit; and
   operating the drive unit in accordance with the control signals to actuate the first and second active tools in unison to pierce a wall of the anatomical vessel, pierce the stent, and secure the stent to an inner wall of the anatomical vessel using the stitch.

2. The method of claim 1, wherein the control signals are conveyed from the remote controller to the drive unit in response to user commands.

3. The method of claim 2, wherein the user commands are movements made at a user interface that correspond to movements of the medical instrument.

4. The method of claim 1, wherein the second medical instrument is introduced within the patient through a natural body orifice of the patient or percutaneously.

5. The method of claim 1, wherein the first and second medical instruments are introduced into the patient by operating the drive unit in accordance with the control signals.

6. The method of claim 1, the stent being introduced by operating the drive unit in accordance with the control signals to introduce the stent adjacent the anatomical vessel.

7. The method of claim 1, further comprising operating the drive unit in accordance with the control signals to advance the second medical instrument within the anatomical vessel.

8. The method of claim 1, wherein the first and second tools are sewing tools that are controlled to stitch the stent to the inner wall of the anatomical vessel.

9. The method of claim 1, wherein the anatomical vessel is a blood vessel.

10. The method of claim 9, wherein the blood vessel is an abdominal aorta.

11. The method of claim 1, wherein first and second ends of the stent are stitched to respective first and second portions of the inner wall of the anatomical vessel by piercing the first and second portions of the inner wall and the first and second ends of the stent.

12. The method of claim 1, the first active tool comprising a needle end effector that pierces the anatomical vessel and the stent and advances a suture through the anatomical vessel and the stent, and the second active tool comprising a hook end effector that receives the suture to stitch together the stent and the anatomical vessel from within the anatomical vessel.

13. The method of claim 1, wherein a stent defining a plurality of slots is introduced into the anatomical vessel.

14. The method of claim 1, wherein introducing the first medical instrument and the second medical instrument comprises introducing a first medical instrument and a second medical instrument each instrument comprising
a shaft;
a flexing section extending from a distal end of the shaft and being controllably bendable, the flexing section defining a plurality of diametrically disposed slots on opposite sides of the flexing section thereby defining respective spaced ribs, the plurality of slots and spaced ribs being structurally configured for controllable bending of the flexing section in a first plane with a first degree of freedom; and
a wrist extending from a distal end of the flexing section and being controllably rotatable about a first axis in a second plane with a second degree of freedom, the first and second planes being substantially perpendicular to each other, the method further comprising:
controllably bending the flexing section within the first plane; and
controllably bending the wrist within the second plane.

15. The method of claim 14, wherein introducing the first medical instrument and the second medical instrument comprises introducing a first medical instrument and a second medical instrument each instrument further comprising
a link extending from a distal end of the wrist and being controllably rotatable about a second axis in a third plane with a third degree of freedom;
an active tool extending from a distal end of the link, the active tool being movable within the link.

16. The method of claim 14, the wrist comprising a fixed wrist pivot, wherein rotation of the fixed wrist pivot is limited to rotation about the first axis in the second plane substantially perpendicular to the first plane, the method further comprising:
controllably bending the fixed wrist pivot within the second plane.

17. The method of claim 14, the wrist comprising flexible wrist comprising alternating ridges configured for universal controllable wrist bending, the method further comprising:
controllably bending the flexible wrist pivot within multiple planes.

18. The method of claim 14, the flexible wrist comprising a series of spaced arcuate ribs disposed in parallel and extending circumferentially at least partially around an outer portion of the flexible wrist, wherein a plane of each arcuate rib extends substantially orthogonally to a longitudinal axis of the flexible wrist.

19. The method of claim 18, the plurality of arcuate ribs being spaced apart from each other by respective alternating ridges.

20. The method of claim 19, the ridges alternating every 90 degrees such that each ridge extends across only two arcuate ribs.

21. The method of claim 19, the alternating ridges being substantially parallel to a central axis defined by the flexible wrist, respective outer surfaces of the plurality of arcuate ribs and the alternating ridges defining an outer surface of the flexible wrist.

* * * * *